United States Patent [19]
Balch

[11] Patent Number: 6,083,763
[45] Date of Patent: Jul. 4, 2000

[54] MULTIPLEXED MOLECULAR ANALYSIS APPARATUS AND METHOD

[75] Inventor: William J. Balch, Woodlands, Tex.

[73] Assignee: Genometrix Inc., The Woodlands, Tex.

[21] Appl. No.: 09/002,170

[22] Filed: Dec. 31, 1997

Related U.S. Application Data

[60] Provisional application No. 60/034,627, Dec. 31, 1996.

[51] Int. Cl.[7] .................................................. G01N 33/543
[52] U.S. Cl. ............................... 436/518; 422/62; 422/63; 422/67; 422/68.1; 422/81; 422/105; 422/112; 435/6; 435/286.1; 435/286.6; 435/286.5; 436/43; 436/50; 436/524; 436/525; 436/527; 436/531
[58] Field of Search ................................. 422/62, 63, 67, 422/68.1, 81, 105, 112; 435/286.1, 286.6, 286.5, 6; 436/518, 524, 525, 527, 531, 43, 50

[56] References Cited

U.S. PATENT DOCUMENTS 4,883,760 11/1989 Heelies .
5,556,762 9/1996 Pinilla et al. .

FOREIGN PATENT DOCUMENTS

| | | |
|---|---|---|
| WO 86/00991 | 2/1986 | WIPO . |
| WO 94/11530 | 5/1994 | WIPO . |
| WO 95/35505 | 9/1995 | WIPO . |
| WO 97/19749 | 6/1997 | WIPO . |

OTHER PUBLICATIONS

Fodor et al, "Light directed spatially addressable parallel chemical systesis", *Science* Feb. 15, 1991, vol. 251 at 767–773.

*Primary Examiner*—Christopher L. Chin
*Attorney, Agent, or Firm*—Fish & Richardson P.C.

[57] ABSTRACT

A method and apparatus for analyzing molecular structures within a sample substance using an array having a plurality of test sites upon which the sample substance is applied. The invention is also directed to a method and apparatus for constructing molecular arrays having a plurality of test sites. The invention allows for definitive high throughput analysis of multiple analytes in complex mixtures of sample substances. A combinatorial analysis process is described that results in the creation of an array of integrated chemical devices. These devices operate in parallel, each unit providing specific sets of data that, when taken as a whole, give a complete answer for a defined experiment. This approach is uniquely capable of rapidly providing a high density of information from limited amounts of sample in a cost-effective manner.

27 Claims, 24 Drawing Sheets

MULTIPLEXED MOLECULAR ANALYSIS APPARATUS AND METHOD

This application is based on US provisional application 60/034,627, filed Dec. 31, 1996, incorporated herein by reference.

STATEMENT AS TO FEDERALLY SPONSORED RESEARCH

This invention was made at least in part with funds from the National Aeronautics and Space Administration, Grant Number NAGW 4530.

TECHNICAL FIELD

This invention relates to a multiplexed molecular analysis apparatus and method for the detection and quantification of one or more molecular structures in a sample.

BACKGROUND

It is very desirable to rapidly detect and quantify one or more molecular structures in a sample. The molecular structures typically comprise ligands, such as antibodies and anti-antibodies. Ligands are molecules which are recognized by a particular receptor. Ligands may include, without limitation, agonists and antagonists for cell membrane receptors, toxins, venoms, oligosaccharides, proteins, bacteria and monoclonal antibodies. For example, DNA or RNA sequence analysis is very useful in genetic and infectious disease diagnosis, toxicology testing, genetic research, agriculture and pharmaceutical development. Likewise, cell and antibody detection is important in numerous disease diagnostics.

In particular, nucleic acid-based analyses often require sequence identification and/or analysis such as in vitro diagnostic assays and methods development, high throughput screening of natural products for biological activity, and rapid screening of perishable items such as donated blood, tissues, or food products for a wide array of pathogens. In all of these cases there are fundamental constraints to the analysis, e.g., limited sample, time, or often both.

In these fields of use, a balance must be achieved between accuracy, speed, and sensitivity in the context of the constraints mentioned earlier. Most existing methodologies are generally not multiplexed. That is, optimization of analysis conditions and interpretation of results are performed in simplified single determination assays. However, this can be problematic if a definitive diagnosis is required since nucleic acid hybridization techniques require prior knowledge of the pathogen to be screened. If symptoms are ambiguous, or indicative of any number of different disease organisms, an assay that would screen for numerous possible causative agents would be highly desirable. Moreover, if symptoms are complex, possibly caused by multiple pathogens, an assay that functioned as a "decision tree" which indicated with increasing specificity the organism involved, would be of high diagnostic value.

Multiplexing requires additional controls to maintain accuracy. False positive or negative results due to contamination, degradation of sample, presence of inhibitors or cross reactants, and inter/intra strand interactions should be considered when designing the analysis conditions.

Conventional Technologies and Limitations

Sanger Sequencing

Of all the existing techniques, one of the most definitive is the traditional Sanger sequencing technique. This technique is invaluable for identifying previously unknown or unsuspected pathogens. It is also valuable in determining mutations that confer drug resistance to specific strains of disease organisms. These analyses are generally research oriented. The end result of this research, e.g., sequence determination of a specific pathogen, can be used to design probes for identification applications in a clinical setting.

However, there are constraints to employing this technique in a clinical lab. The primary constraints are cost and throughput due to the inherent labor intensive procedures, requiring multiple steps to be performed by skilled personnel. For example, typical analysis usually requires more than a day for completion. Of more concern is the potential for ambiguity when multiple strains of a pathogen are present in one sample. Virulence of the pathogen is often determined by the strain. An example is HPV, also known as human papilloma virus. Seventy strains of HPV are commonly known to exist. Two strains, in particular, are strongly associated with an increased risk of cervical cancer, hence the aggressiveness of treatment or screening for malignancy is determined by the presence of an HPV strain. Multiple strains cause indeterminate results when using sequencing methodologies. The ideal assay would be multiplexed with the selectivity to identify all strains involved.

Blotting Techniques

Blotting techniques, such as those used in Southern and Northern analyses, have been used extensively as the primary method of detection for clinically relevant nucleic acids. The samples are prepared quickly to protect them from endogenous nucleases and then subjected to a restriction enzyme digest or polymerase chain reaction (PCR) analysis to obtain nucleic acid fragments suitable for the assay. Separation by size is carried out using gel electrophoresis. The denatured fragments are then made available for hybridization to labeled probes by blotting onto a membrane that binds the target nucleic acid. To identify multiple fragments, probes are applied sequentially with appropriate washing and hybridization steps. This can lead to a loss of signal and an increase in background due to non-specific binding. While blotting techniques are sensitive and inexpensive, they are labor intensive and dependent on the skill of the technician. They also do not allow for a high degree of multiplexing due to the problems associated with sequential applications of different probes.

Microplate Assays

Microplate assays have been developed to exploit binding assays, e.g., an ELISA assay, receptor binding and nucleic acid probe hybridization techniques. Typically, with one microplate, e.g., micro-well titer plate, only one reading per well can be taken, e.g., by light emission analysis. These assays function in either one of two ways: (1) hybridization in solution; or (2) hybridization to a surface bound molecule. In the latter case, only a single clement is immobilized per well. This, of course, limits the amount of information that can be determined per unit of sample. Practical considerations, such as sample size, labor costs, and analysis time, place limits on the use of microplates in multiplex analyses. With only a single analysis, reaction, or determination per well, a multiple pathogen screen with the appropriate controls would consume a significant portion of a typical 96 well format microplate. In the case where strain determination is to be made, multiple plates must be used. Distributing a patient sample over such a large number of wells becomes highly impractical due to limitations on available sample material. Thus, available patient sample volumes inherently limit the analysis and dilution of the sample to increase volume seriously affects sensitivity.

Polymerase Chain Reaction

Although, the polymerase chain reaction (PCR) can be used to amplify the target sequence and improve the sensitivity of the assay, there are practical limitations to the number of sequences that can be amplified in a sample. For example, most multiplexed PCR reactions for clinical use do not amplify more than a few target sequences per reaction. The resulting amplicons must still be analyzed either by Sanger sequencing, gel electrophoresis, or hybridization techniques such as Southern blotting or microplate assays. The sample components, by PCR's selective amplification, will be less likely to have aberrant results due to cross reactants. This will not be totally eliminated and controls should be employed. In addition, PCR enhances the likelihood of false positive results from contamination, thus requiring environmental controls. PCR controls must also include an amplification positive control to ensure against false negatives. Inhibitors to the PCR process such as hemoglobin are common in clinical samples. As a result, the PCR process for multiplexed analysis is subject to most of the problems outlined previously. A high density of information needs to be acquired to ensure a correct diagnostic determination. Overall, PCR is not practical for quantitative assays, or for broad screening of a large number of pathogens.

Probe-Based Hybridization Assays

Recently, probe hybridization assays have been performed in array formats on solid surfaces, also called "chip formats." A large number of hybridization reactions using very small amounts of sample can be conducted using these chip formats thereby facilitating information rich analyses utilizing reasonable sample volumes.

Various strategies have been implemented to enhance the accuracy of these probe-based hybridization assays. One strategy deals with the problems of maintaining selectivity with assays that have many nucleic acid probes with varying GC content. Stringency conditions used to eliminate single base mismatched cross reactants to GC rich probes will strip AT rich probes of their perfect match. Strategies to combat this problem range from using electrical fields at individually addressable probe sites for stringency control to providing separate micro-volume reaction chambers so that separate wash conditions can be maintained. This latter example would be analogous to a miniaturized microplate. Other systems use enzymes as "proof readers" to allow for discrimination against mismatches while using less stringent conditions.

Although the above discussion addresses the problem of mismatches, nucleic acid hybridization is subject to other errors as well. False negatives pose a significant problem and are often caused by the following conditions:

1) Unavailability of the binding domain often caused by intra-strand folding in the target or probe molecule, protein binding, cross reactant DNA/RNA competitive binding, or degradation of target molecule.
2) Non-amplification of target molecule due to the presence of small molecule inhibitors, degradation of sample, and/or high ionic strength.
3) Problems with labeling systems are often problematic in sandwich assays. Sandwich assays, consisting of labeled probes complementary to secondary sites on the bound target molecule, are commonly used in hybridization experiments. These sites are subject to the above mentioned binding domain problems. Enzymatic chemiluminescent systems are subject to inhibitors of the enzyme or substrate and endogenous peroxidases can cause false positives by oxidizing the chemiluminescent substrate.

SUMMARY

The instant invention provides for both a multiplexed environment to rapidly determine optimal assay parameters, as well as a fast, cost-effective, and accurate system for the quantitative analysis of target analytes, thereby circumventing the limitations of single determination assays. The optimization of a multiplexed assay can be carried out by experimental interrogation to determine the appropriate solution conditions for hybridization and stringency washes. The development of these optimal chemical environments will be highly dependent on the characteristics of the array of bound capture probe molecules, their complementary target molecules, and the nature of the sample matrix.

Multiplexed molecular analyses are often required to provide an answer for specific problems. For example, determining which infectious agent out of a panel of possible organisms is causing a specific set of disease symptoms requires many analyses. Capture probe arrays offer the opportunity to provide these multivariate answers. However, the use of single probe array platforms does not always provide enough information to solve these kinds of problems. Recent innovative adaptations of proximal charge-coupled device (CCD) technology has made it feasible to quantitatively detect and image molecular probe arrays incorporated into the bottom of microplate wells. This creates a high throughput platform of exceptional utility, capable of addressing several applications with very complex analysis parameters.

Uses

The multiplexed molecular analysis system of the instant invention is useful for analyzing and quantifying several molecular targets within a sample substance using an array having a plurality of biosites upon which the sample substance is applied. For example, this invention can be used with microarrays in a microplate for multiplexed diagnostics, drug discovery and screening analysis, gene expression analysis, cell sorting, and microorganic monitoring (see examples below for each use).

Proximal CCD Imaging with Multiplexed Arrays

One application of the microplate based arrays of this invention is in parallel processing of a large number of samples. Large clinical labs process thousands of samples a day. A microplate configured with a four by four (4×4) matrix of biosites in each of the 96 wells would be able to perform a total of 1536 nearly simultaneous tests is from 96 different patient samples utilizing the proximal CCD imager as illustrated in FIG. 1. FIG. 1 is a diagram showing a multiplexed molecular analysis detection/imaging system. Moreover, a microplate configured with 15×15 arrays of probe elements in each of 96 wells enables a total of 21,600 nearly simultaneous hybridization analyses, which becomes significant for analyzing gene expression from specific cells.

Throughput is also important when screening natural products for biological activity. A matrix of biosites that model binding sites of interest may be placed in the bottom of each well and interrogated with an unknown product. Thousands of molecules may be screened per day against these biosite arrays.

Creation of Hierarchical Arrays

Another use of the microplate based arrays is for the creation of hierarchical arrays for complex analyses. In this format, multiple arrays operate in parallel to provide an answer to a complex assay. The example of the diagnostic assay provided in the Background section illustrates some of the parameters which should be considered in order to provide an accurate result. For any specific analysis, a set of probe elements must be chosen. The selected probe elements should be able to selectively associate with defined targets without significant cross association to other macromolecules expected from either the patient or other organisms commonly associated with a specific sample type. Controls must be designed to prevent false positive or negative results from the sources outlined in the Background section. Once this is done, a combinatorial process can be used to identify the optimal association and selectivity conditions for the defined analysis. For nucleic acid applications, these conditions are highly dependent on the capture probe length and composition, target base composition, and sample matrix. The number of arrays to be used depends on a number of different factors, e.g., the controls to be implemented and the differences in base composition of the capture probes. Ultimately, a set of integrated chemical devices emerge that can rapidly, efficiently, and accurately provide an answer for the molecular analysis of interest.

Another use of the hierarchical arrays and the reaction vessel based arrays would be for screening, samples for a broad range of possible targets. In one case, a diagnostic test is performed to search for the cause of a defined set of symptoms. In most cases this narrows the range of possible organisms to a small number. Conversely, to screen donated blood or tissue for a broader range of disease organisms, a decision tree approach could be employed. Here an initial array or set of arrays could be chosen to screen for broader classes of pathogens using probes for highly conserved nucleic acid regions. Results from this would indicate which additional array sets within the microplate to sample next, moving to greater and greater specificity. If enough sample is available, as might be the case with donated blood or tissue, all of the decision tree elements could be interrogated simultaneously. If sample quantity is limiting, the approach could be directed in a serial fashion.

Assay development for any multiplex analysis is time consuming. The microplate based arrays as described herein can be used to speed the process for capture probe/target binding or hybridization. A defined array can be deposited into each well of a microplate and then the association reactions are carried out using "gradients" of conditions that vary in two dimensions. For example, consider a 96 well microplate containing nucleic acids arranged in 8 rows by 12 columns. In one step of the optimization, the effects of pH on various substrate compositions might be examined to see how this affects hybridization specificity. Twelve different pH's, one for each column, and 8 different surface chemistries, one for each row could be used under otherwise identical hybridization conditions to measure the effects on hybridization for each capture probe/target element in the array. This type of analysis will become essential as array technology becomes widely used and is amenable to any receptor/ligand binding type experiment.

The hierarchical array format, consisting of defined sets of arrays with individually optimized chemical environments functioning in parallel to provide an answer to a complex analysis, can be implemented in other ways. Instead of a batch process, where a series of analysis sets are present in each microplate, a hierarchical array analysis set can be fashioned into a flow cell arrangement. This would be specific to a particular analysis and consist of the appropriate array sets and the necessary fluidics to take a single sample and deliver the appropriate aliquot to each array in the set. The fluidics will deliver the appropriate association and wash fluids to perform the reactions, as defined for each array in the set.

Advantages

The multiplexed molecular analysis system of the instant invention has many advantages over the conventional systems. Some of these advantages are discussed below.

High Throughput

Multiple DNA/RNA probe arrays can be fabricated in the bottom of 96 well microtiter plates which offer the potential of performing 1,536 (96×16) to 21,600 (96×225) hybridization tests per microtiter plate. Each well will contain a probe array of N elements dispensed onto plastic or glass and bonded to the microtiter plate. Moreover, by coupling the microtiter trays to a direct (lensless) CCD proximal/imager, all 1,536 to 21,600 hybridization tests can be quantitatively accessed within seconds at room temperature. Such proximal CCD detection approach enables unprecedented speed and resolution due to the inherently high collection efficiency and parallel imaging operation. The upper limit to the hybridization tests per microtiter plate exceeds 100,000 based on a 100 $\mu$m center-to-center spacing of biosites.

Low Cost

Since the capture probe volumes dispensed on the reaction substrate can be limited to about 50 picoliters (pL), only 150 nanoliters (nL) of capture probe reagent is required to produce over 1,500 distinct binding tests. The dispensing of the probe arrays on plastic rolls or on thin glass sheets can be efficiently performed in an assembly-line fashion with a modular ink-jet or capillary deposition system.

Automated Operation

The multiplexed assay can be designed in a standard 96 well microtiter plate format for room temperature operation to accommodate conventional robotic systems utilized for sample delivery and preparation. Also, the proximal CCD-based imager with a graphical user interface will enable the automation of the parallel acquisition of the numerous hybridization test results. The CCD imaging system software provides automated filtering, thresholding, labeling, statistical analysis and quantitative graphical display of each probe/target binding area within seconds.

Versatility

The proximal CCD detector/imager utilized in a particular embodiment of the multiplexed molecular analysis system accommodates numerous molecule labeling strategies including fluorescence, chemiluminescence and radioisotopes. Consequently, a single instrument can be employed for a variety of reporter groups used separately or together in a multiplexed manner for maximal information extraction.

High Resolution

The accompanying proximal CCD detector/imager offers high spatial and digital resolution. In the preferred embodiment, CCD pixel sizes of approximately 25×25 $\mu m^2$ will support the imaging of hundreds to thousands of individual biosites on a reaction substrate. Together with 16 bit digital imaging, a highly quantitative image of the high density of biosites is achieved.

Fast Time-to-Market

Since the approach outlined is based on previously demonstrated proximal CCD detection and imaging coupled with microarrays dispensed in conventional sized microtiter plates, the overall molecular analysis system is expected to provide a fast time-to-market solution to complex multicomponent molecular-based analyses.

Overall, the invention disclosed provides a method and apparatus for both a multiplexed environment to rapidly determine the optimal assay parameters as well as a fast, cost-effective, and accurate system for the quantitative analysis of molecules, thereby circumventing the limitations of single determination assays.

Other features and advantages of the invention will be apparent from the following detailed description, and from the claims.

DETAILED DESCRIPTION

Definitions

Figure 1:
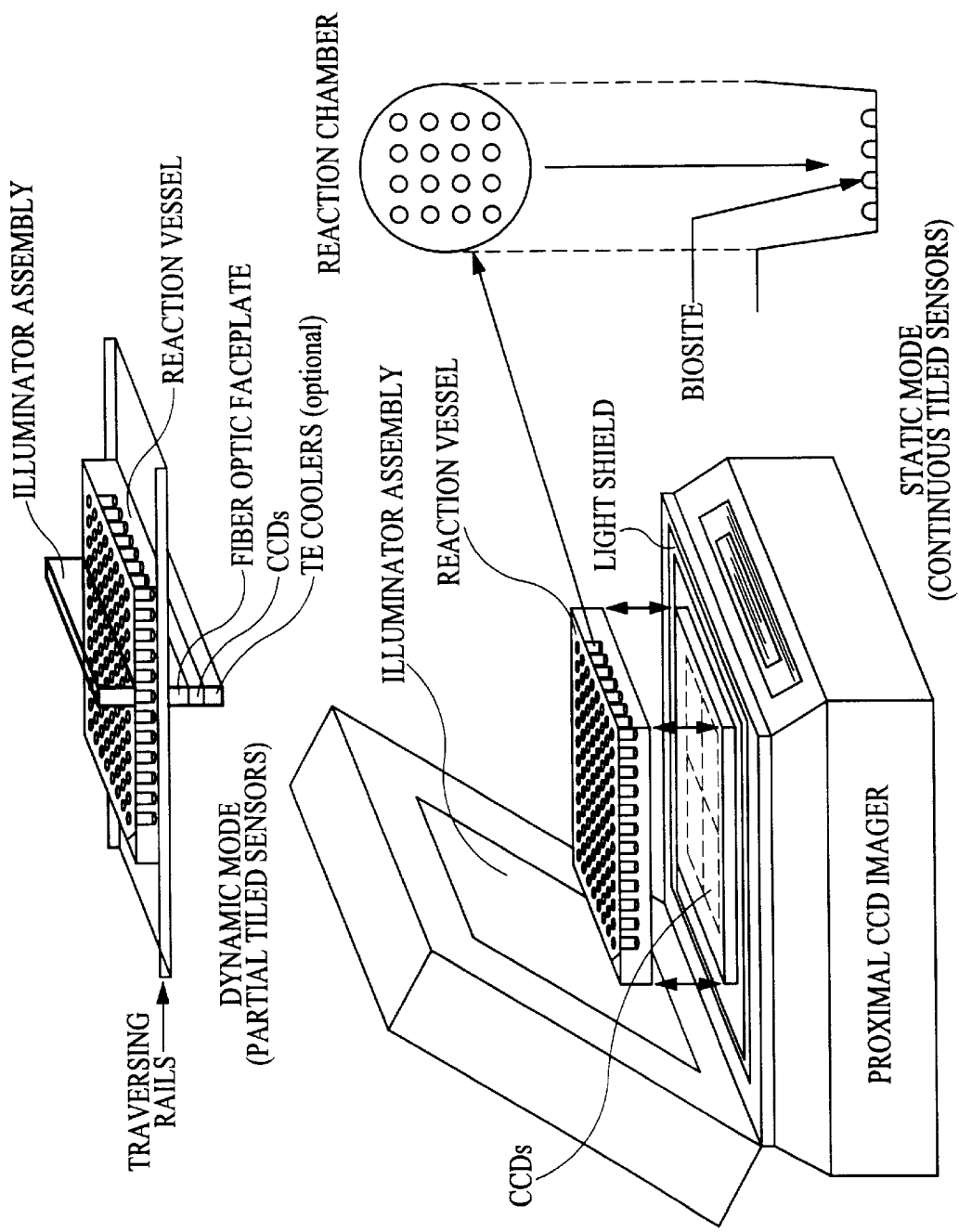
FIG. 1 is a diagram showing a multiplexed molecular analysis detection/imaging system.

For the purpose of this invention, different words and phrases are defined as follows:

By "target molecules or target analyte" is meant the molecules of interest in a substance which are to be interrogated by binding to the capture probes immobilized in an array.

By "mRNA target molecule or mRNA target analyte" is meant a substance containing identical mRNA components or a mixture of disparate mRNAs.

By "capture probe, probe molecules or probes" is meant the molecules which are deposited as biosites onto the reaction substrate for interrogating the target molecules. Probes are meant to include nucleic acids, DNA, RNA, receptors, ligands, antibodies, anti-antibodies, antigens, proteins, and also small chemical compounds such as drugs, haptens, or peptides.

The term "hapten binding polypeptide" includes intact antibody molecules as well as fragments thereof, such as Fab, $F(ab')_2$, Fv, single chain antibody (SCA), and single complementary-determining region (CDR). For purposes of the invention, "hapten" and "epitope" are considered interchangeable.

The term "array" refers to a two-dimensional spatial grouping or an arrangement.

By "hierarchical array" is meant an array arranged in an hierarchy or arranged in a graded or ranked series. Examples of different "hierarchical arrays" comprising the multiplexed assay of the invention include, but are not limited to, an array of a 96 well microtiter plate, wherein there are N probe sites or biosites per well, wherein there are $10^7$ to $10^{10}$ molecules for each probe site or biosite, wherein an array of M depositors are used to deposit probes in each probe site onto the film substrate that forms the bottom of the well in a 96 microtiter well reaction chamber. The depositors can deposit the probes via many different mechanisms, e.g., ink-jet deposition, capillary, and photolithography.

The term "probe arrays" refers to the array of N different biosites deposited on a reaction substrate which serve to interrogate mixtures of target molecules or multiple sites on a single target molecule administered to the surface of the array.

The term "oligonucleotide probe arrays" refers to probe arrays wherein the probes are constructed of nucleic acids.

By "charge coupled device," also referred to as CCD, is meant a well-known electronic device which outputs an electrical signal proportional to the incident energy upon the CCD surface in a spatially addressable manner.

The term "CCD proximal detection" refers to the use of CCD technology for detection and imaging in which the CCD is proximal to the sample to be analyzed, thereby avoiding the need for conventional lenses.

By "ligands" is meant molecules which are recognized by a particular receptor. "Ligands" may include, without limitation, agonists and antagonists for cell membrane receptors, toxins, venoms, oligosaccharides, proteins, bacteria and monoclonal antibodies.

By "multiplexed" is meant many or a multiple number.

By "multiplexed diagnostic assay" is meant a method for performing in parallel a large set or number of diagnostic assays. Thus a set of parallel reactions can be handled with the same effort as a single sample in previously described methods. Hence, a greater number of assays can be handled within a fixed period of time. The parallel set of reactions or multiplexed assay must be deciphered at the end of the process. This is done by labeling or tagging the biosite, as defined herein.

The term "reaction vessel" refers to an array of reaction chambers as defined below. An example of a reaction vessel is a 96 well microtiter plate.

By "reaction chamber" is meant the environment in which the hybridization or other binding association takes place. Commercially available reaction vessels contain at least one reaction chamber, but can contain 8, 24, 96 or 384 reaction chambers. For this invention, "reaction chamber(s)," "well(s)," "reaction site(s)," "reaction substrate(s)," "array hybridization site(s)," "hybridization chamber(s)," and "hybridization well(s)," are used interchangeably. An example of a reaction chamber is one of the 96 microtiter wells in a 96 well microtiter plate.

By "biosite" is meant the biological molecules or capture probes that are deposited on the top surface of the reaction substrate, or base material. Under appropriate conditions, an association or hybridization can occur between the capture probe and a target molecule. The component strands of the biological molecule form the biosite since there is the potential of a reaction occurring between each component strand of the biological molecule and the target molecule. For example, each reaction chamber can contain at least one biosite. The maximum number of biosites per reaction chamber will depend on the size of the reaction vessel and on the practical optical resolution of the accompanying detector/imager. For example, an array of 16 (4×4 array) biosites may be deposited on the hybridization substrate or base material that eventually forms the bottom of the entire reaction vessel. Each biosite comprises a circle of approximately 25–200 microns ($\mu$m) in diameter. Thus, for a 16 biosite array, each of the 16×200 $\mu$m diameter area contains a uniform field of probes attached to the hybridization substrate (base material) in a concentration which is highly dependent on the probe size and the well size. Each 25–200 $\mu$m diameter area can contain millions of probe molecules. Also, each of the 16 different biosites (probe sites) can contain one type of probe. Thus, 16 different probe types can be assayed in an array containing 16 biosites (4×4 array) per reaction chamber. As another example, four separate 10×10 arrays (400 biosites) can be generated to fit into one well of a 96 well microtiter plate with sufficient spacing between each of the 400 biosites. For this 10×10 format, 400 hybridization experiments are possible within a single reaction chamber corresponding to 38,400 (96×400) assays/hybridization that can be performed nearly simultaneously.

By "reaction substrate" is meant the substrate that the biosites or probe sites are deposited on by using the depositors. Examples of "reaction substrates" include, without limitation, nylon membrane, polypropylene, polystyrene, vinyl, other plastics and glass.

By "modular deposition array" is meant an array of depositors. The number of depositors depends primarily on the dimensions of the reaction substrate. For example, there can be four depositors fitted next to each other, staggered regarding the front to back position of each depositor. Each depositor can be directly coupled to a housing reservoir. The housing reservoir holds a solution, e.g., a solution containing a desired probe at an appropriate concentration. The number of injection mechanisms again depends on the design of the depositor, e.g., ranging from one to several injection mechanisms per depositor.

By "array formats on solid surfaces" is meant chip formats or microarrays.

By "throughput" is meant the number of analyses completed in a given unit of time.

By "decision tree approach" is meant a sequential routing approach in which at each step an assessment is made which directs the subsequent step.

By "hybridization detection" is meant to include, without limitation, a means of two or more components to interact through hybridization, an association, linking, coupling, chemical bonding, covalent association, lock and key association, and reaction. For the purpose of this invention, these terms are used interchangeably.

By "methods of detecting (or detection) the association/hybridization" is meant to include, without limitation, fluorescent labeling, radioisotope labeling, chemiluminescence labeling, bioluminescence labeling, colorimetric labeling. Labeling can be achieved by one of the many different methods known to those with skill in this art.

The term "luminescence" refers to, without limitation, electrical (electro), chemical, fluorescence, phosphorescence, bioluminescence, and the like. However, for this invention, electrochemiluminescence or electrical chemiluminescence (ECL) labeling is included as another method of detection which does not require a wash step to remove excess target molecules from the solution, and is highly sensitive. For the electrochemiluminescence or electrical chemiluminescence method of detection, once hybridization/association has occurred and a voltage has been applied, only the labeled target molecules associated with the biosite will emit light and be detected. The residual excess label in the solution not associated with the biosite will therefore not emit light.

This application is related to the following pending United States Patent Applications, incorporated herein by reference: U.S. Ser. No. 07/794,036 entitled "Method and Apparatus for Molecular Detection" filed Nov. 11, 1991, U.S. Ser. No. 08/353,957 entitled "Multiple Molecule Detection Apparatus" issued Jul. 2, 1996, U.S. Ser. No. 08/457,096 entitled "Multiple Molecule Detection Method" filed, Jun. 1, 1995, U.S. Ser. No. 07/872,582 entitled "Optical and Electrical Methods and Apparatus for Molecule Detection" filed Apr. 23, 1992, U.S. Ser. No. 08/511,649 entitled "Optical and Electrical Methods and Apparatus for Molecule Detection" filed Aug. 7, 1995, and U.S. Ser. No. 08/201,651 entitled "Method and Apparatus for Detection and Imaging Particles" filed Feb. 25, 1994.

Overview

The multiplexed molecular analysis system of the invention can be divided into four aspects:

A. Preparing the sample for subsequent association to a probe array within the reaction chamber. This includes all front-end processes such as purification, isolation, denaturation and labeling required to extract the target molecules from the sample.

B. Binding target molecules to the biosites within specialized reaction chambers in sufficient concentrations for association to occur. Following association, non-specific binding of target molecules is often minimized by washing out the reaction chambers.

C. Detecting and/or imaging the association (hybridization) of the target molecules with the biosites within each reaction chamber by proximal detection/imaging.

D. Processing the images to determine information about the target molecules such as the presence and amount of specific molecular constituents within a given sample that leads to the analysis output.

The advantage of the instant invention lies in the particular implementation of the above four procedures/steps, in particular in the method and apparatus for:

STEP 1. Biosite Deposition. Biosite deposition relates to constructing microarrays.

STEP 2. Self Assembling Arrays—Universal Arrays. Creating and constructing self assembling probe arrays or universal arrays enables on-line configuration of the biosites wherein an unvarying probe array (capture probes) is activated by binding to a cognate set of adapters (target probes) to yield a modified probe array which is specifically configured for analysis of a target or target mixture. For this invention, "cognate" is defined for nucleic acids as a sequence which is complementary by the means of Watson-Crick pairing to another sequence.

STEP 3. Molecular Labeling Strategies. Molecular labeling strategies relates to versatile labeling of the target molecules (fluorescence, chemiluminescence, etc.) consistent with proximal large area detection/imaging.

STEP 4. Detection System. A detection system relates to parallel detection and/or imaging in the reaction vessel containing the reaction chambers using a proximal large area detector/imager.

Step 1—Biosite Deposition

Biosite deposition relates to constructing microarrays. There are many different methods that may be used for depositing biosites into/onto the reaction chamber. Three of these approaches are taught below.

1. Ink-Jet Deposition

Ink-jet printing can be employed for printing the biological fluids to form the biosites. This approach provides very low droplet volumes ($\approx$100 pL with 75 $\mu$m diameter spot size) which minimizes reagents used and therefore cost. Moreover, the printing process can be accelerated to thousands of droplets per second, thereby enabling a high throughput production capability for the reaction vessels.

One method useful for this invention utilizes electromechanically driven ink-jets which produce a volumetric change in the fluid by applying a voltage across a piezoelectric material (See Hansell, U.S. Pat. No. 2,512,743, 1950). The volumetric changes causes a subsequent pressure transient in the fluid which can be directed to form a drop on demand (D. Bogg et al., *IBM Jour Res Develop* (1984) 29:214–321.

Individual ink-jet devices can be integrated in a modular fashion to enable the printing of multiple fluids. For example, MicroFab Inc. has developed an ink-jet based DNA probe array printer constructed of eight modular dispensing units, each with an integral 500 mL reservoir independently addressed by respective drive and control electronics.

Figure 2:
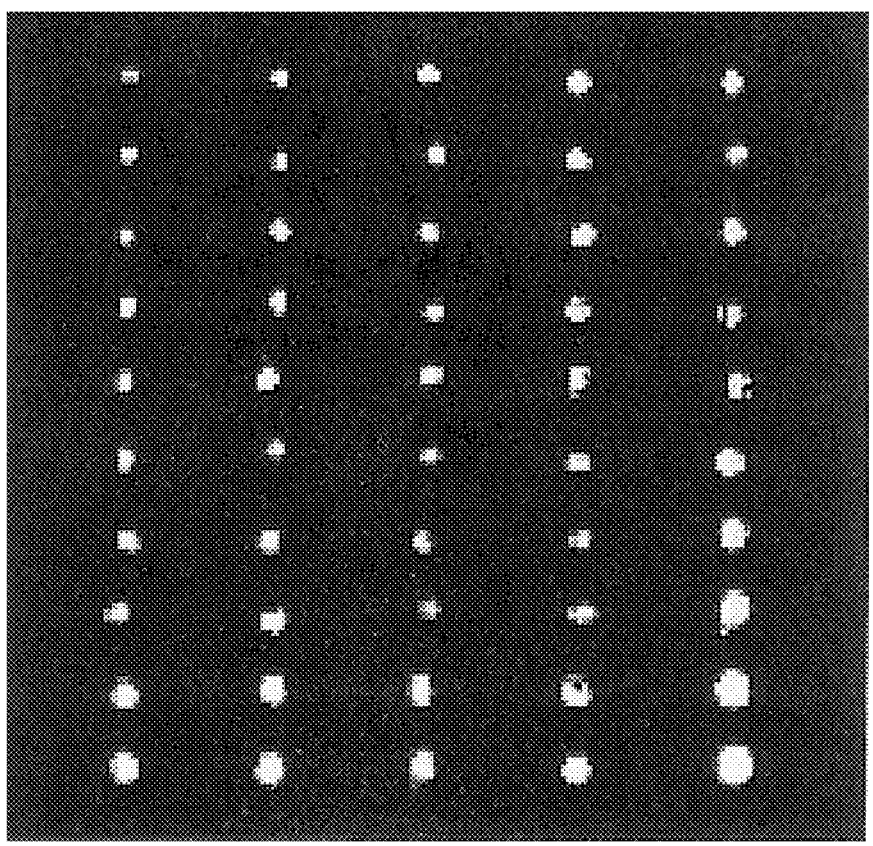
FIG. 2 is a printed computer image obtained with the proximal CCD imager showing deposited DNA probe biosites with ink-jet printing.

FIG. 2 depicts a printed computer image showing DNA probe biosites deposited with ink-jet printing. FIG. 2 illustrates actual biosite deposition whereby an array of 100 DNA probe biosites per 1 $cm^2$ was ink-jet deposited onto a glass substrate. The array consists of alternating columns of match and mismatch 12 mer probes which were subsequently hybridized to a 12 mer single-stranded DNA target. The mismatch columns correspond to an A—A mismatch in the probe/target complex. The actual image was captured within 1 second by the proximal CCD detector/imager described below.

Figure 3:
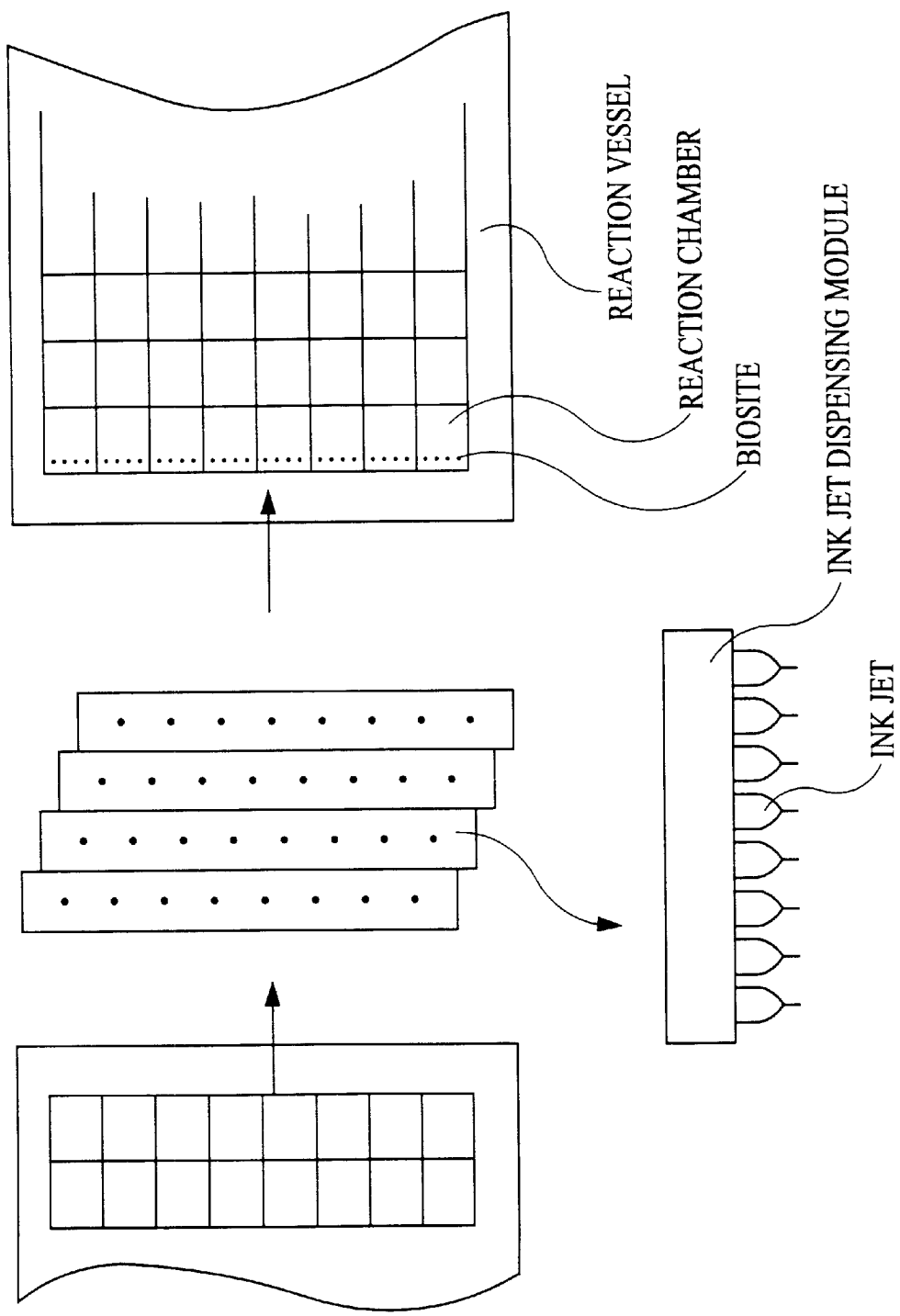
FIG. 3 is a diagram showing the biosite deposition system using staggered ink-jet dispensing modules.

L banks of modular ink-jet devices containing M depositors per module can be assembled in a staggered fashion to print L×M different biosites on the bottom surface of the reaction chambers as illustrated in FIG. 3. FIG. 3 is a diagram showing the biosite deposition system using staggered ink-jet dispensing modules. Here the reaction vessel is moved by a precision motor-controlled stage underneath the ink-jet devices for rapid printing. By constructing additional banks of modular ink-jet devices and/or miniaturizing the individual depositors, an arbitrarily large number of distinct biosites can be printed in the reaction vessels. Alternatively, the printing can be performed on thin substrates such as glass or plastics which are subsequently bonded to form the bottom of the reaction vessels.

2. Capillary Deposition

Figure 4:
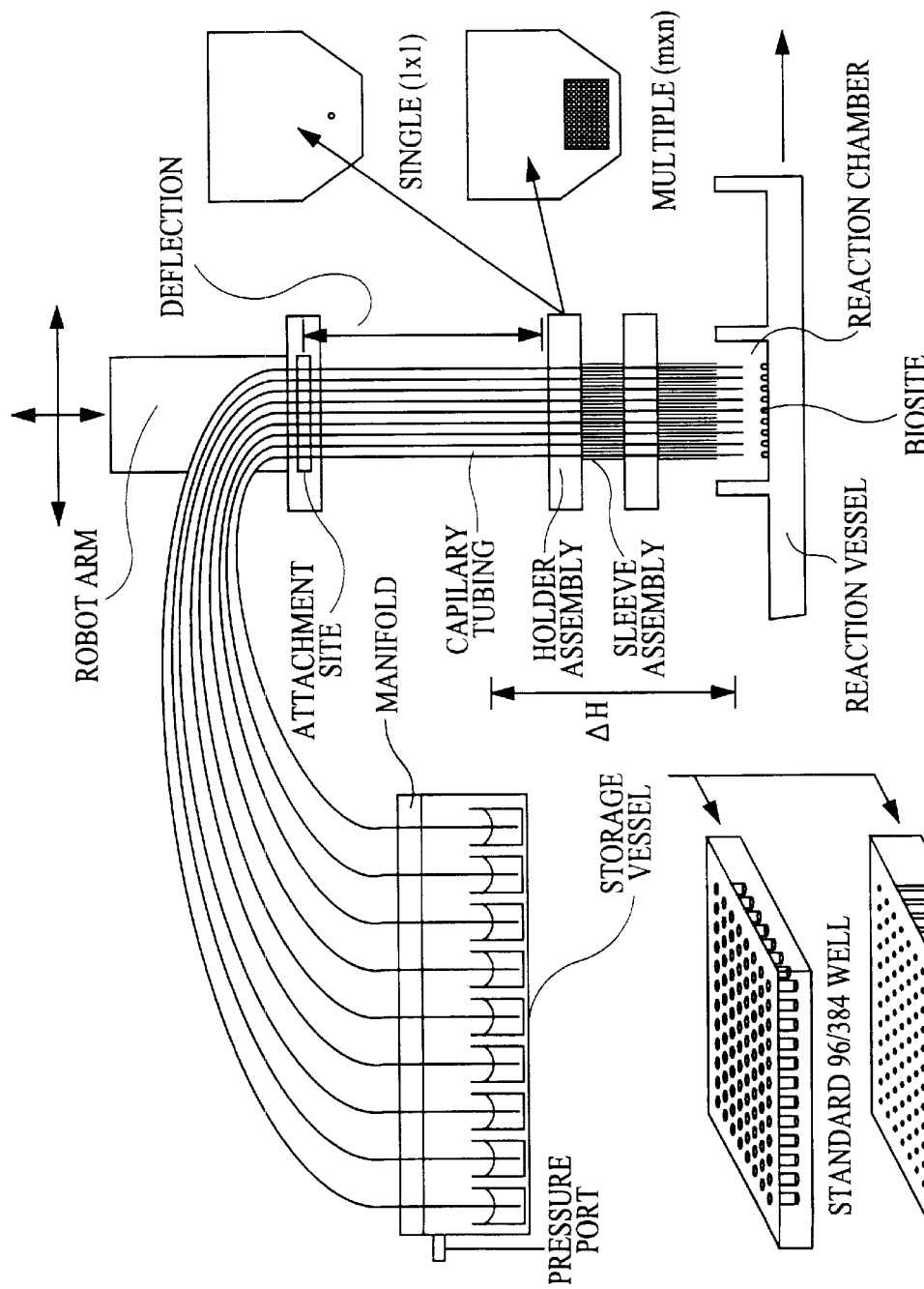
FIG. 4 is a diagram showing the biosite deposition system using multiple capillaries.
Figure 4A:
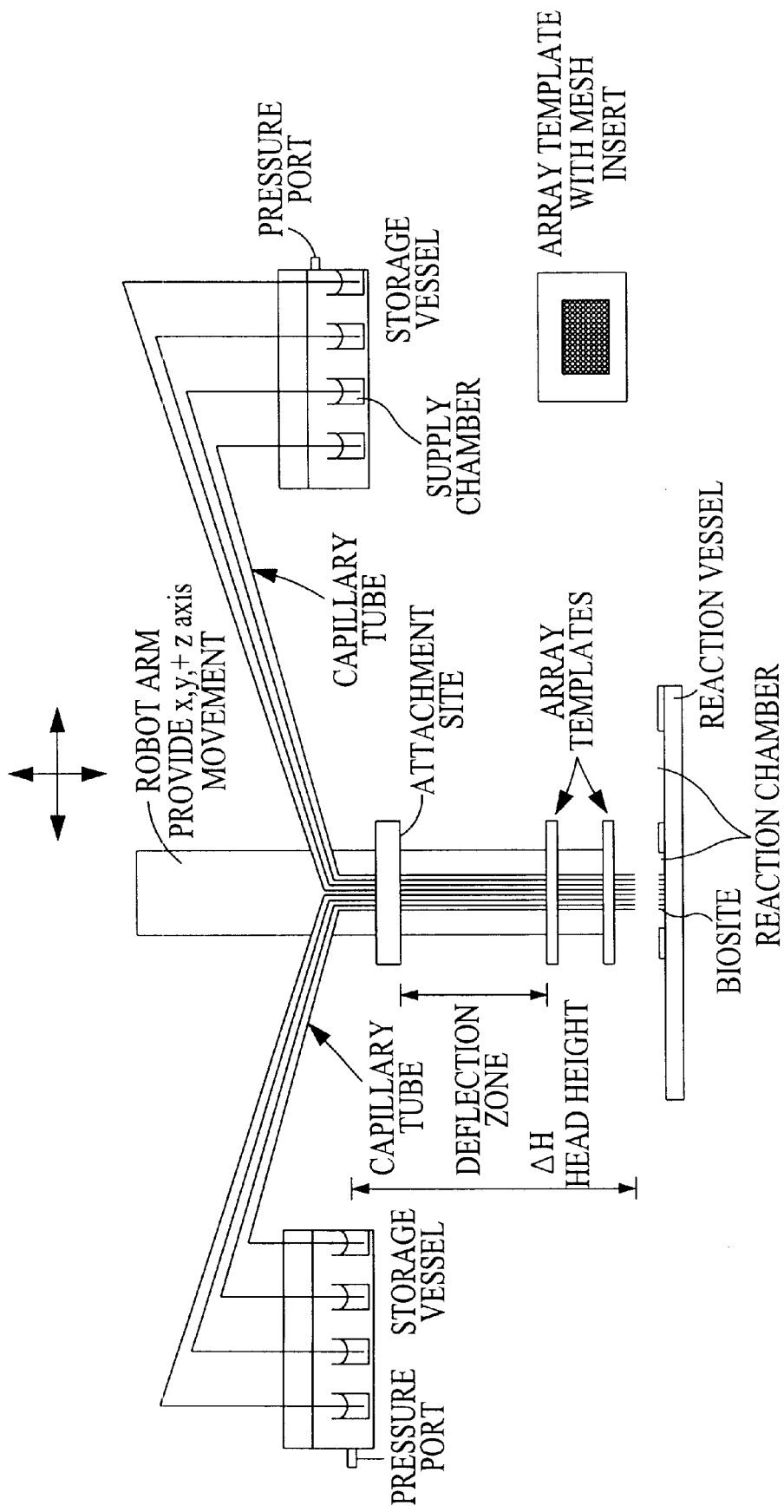
FIG. 4a is a diagram showing biosite deposition with array templates.
Figure 4B:
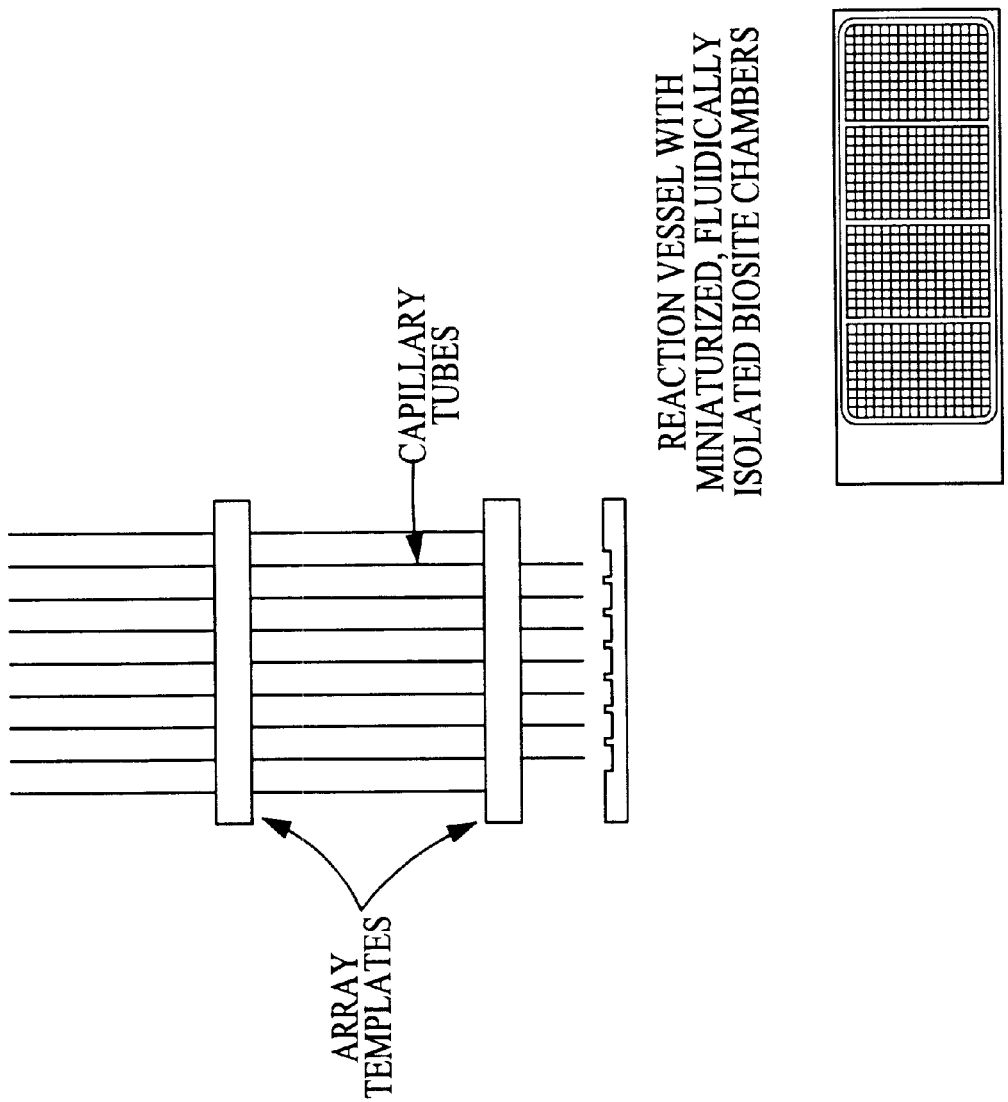
FIG. 4b is a diagram showing biosite deposition into nanoliter wells.

Another approach to biosite deposition involves the use of capillary tubing to dispense small amounts of the biosite solution onto the reaction substrate as illustrated in FIGS. 4, 4a, and 4b. FIG. 4 depicts a biosite deposition system using multiple capillaries. FIG. 4a is a diagram showing biosite deposition with array templates. FIG. 4b is a diagram showing biosite deposition into nanoliter wells. As shown, a storage vessel which contains the appropriate solutions is pressurized momentarily to prime tubes held in appropriate position by a manifold to initiate the capillary dispensing action. With very small inner diameter capillaries (<50 $\mu$m), continuous pressure may be applied. Pressure pulses of varying duration can be utilized to deliver larger volumes of solution. Upon contact with the reaction substrate, the capillary tubes simultaneously deliver small volumes of the biosite solutions at precise locations controlled by spatial arrangement of the bundled capillaries.

In this invention, the storage vessel allows for sampling either from a standard format microtiter plate or a customized plate designed to hold small volumes of liquid, allowing the capillary to efficiently dispense picoliter volumes of liquid to many thousands of biosites with minimal loss to evaporation or possibility of cross contamination.

The lid of the storage vessel holder can be attached to a Z-axis motion control device to allow for automated changes of the biosite solutions contained in the microplates which may be delivered by a robotic arm. This is useful for printing sets of arrays containing large numbers of solutions, such as small molecule libraries used in drug discovery.

Also in this invention, the capillary tubing may be made of fused silica coated with an outer layer of polyimide. These tubes are available commercially in any length with various widths and internal diameters. The preferred dimensions are 80 to 500 $\mu$m outer diameter (OD) and 10 to 200 $\mu$m inner diameter (ID). The capillary bundles may be affixed to a robot arm and held in a precise pattern by threading the capillaries through array templates. An array template is a structure designed to maintain the capillaries in the desired configuration and spacing, and may consist of, without limitation, a metal grid or mesh, a rigidly-held fabric mesh, a bundle of "sleeve" tubes having an inner diameter sufficient to admit the fluid delivery capillaries, or a solid block having holes or channels, e.g., a perforated aluminum block.

The embodiment depicted employs 190 $\mu$m OD capillaries, which are threaded through an attachment site at the top of the printing fixture. The tubes extend down from the attachment site through an area that allows for the capillaries to flex during printing. Below the flex region the capillaries are threaded through an array template or a set of fused silica sleeves held in a grid pattern by the aluminum holder assemblies. The capillary sleeves/array template constitute an important innovation. The array templates/capillary sleeves also allow the capillary tubing to travel smoothly and independently with respect to each other in the vertical axis during printing.

The printing system can print high density probe arrays covering the bottom surface of microplate wells. To accomplish this, the printing system must be able to maintain a precise printing pattern and accommodate irregular surfaces. Rigid tubes could be used to maintain a precise pattern, however, they cannot readily accommodate irregular surfaces. Flexible tubes will print on uneven surfaces but will not maintain a precise printing pattern. The rigid sleeves, which extend below the aluminum holder assembly approximately 2 cm, support the flexible 190 μm OD fused silica capillary tubing and provide the structural rigidity necessary to maintain a precise grid pattern over this distance. The sleeves also allow the 190 μm tubing to travel smoothly in the Z axis during printing. This ability coupled with the flexibility of the small OD capillary tubing allows for successful printing on surfaces that are not completely flat or absolutely perpendicular to the printing fixture. Since the robot arm extends 0.1 mm to 0.3 mm beyond the point where the capillary bundle contacts the surface, the capillaries flex in the deflection zone illustrated in FIG. 4 resulting in total surface contact among all capillaries in the bundle. When the printing fixture withdraws from the substrate, the capillaries straighten, returning to their original positions. The highly parallel nature of the capillary bundle printing technique allows for microarrays containing from two to over 10,000 chemically unique biosites to be created with a single "stamp." The printer can print these arrays at a rate of approximately one per second. This represents a greater than 10-fold increase in speed over existing technologies such as photolithographic in situ synthesis or robotic deposition using conventional load and dispense technology.

In photolithographic microarray synthesis, a series of masks are sequentially applied to build the nucleic acid probes a base at a time. An array of oligonucleotide probes each 12 bases long would require 48 masks (12 nucleotide positions×4 bases). This process takes approximately 16 hours to complete a wafer containing 48 microarrays.

Current robotic microarray printing or gridding systems are universally based on various load and dispense techniques. These techniques can be split into two categories. Active loading systems such as syringe needles or capillaries draw up enough solution to dispense multiple biosites or array elements before returning to reload or collect a new probe solution. Pin style printing or gridding systems can only print one biosite per pin at a time. The pins are dipped into the probe solutions momentarily and the amount of solution adhering to the pin is sufficient to print a single biosite. Both categories have limitations that are resolved by the capillary bundle printing system described herein.

Production capacity is a primary constraint in microarray manufacturing, limiting the use of microarrays in high volume applications such as drug discovery due to the cost and limited availability. For photolithographic in situ synthesis, the constraint is the number of individual masks that must be applied to create an array of probes with the necessary length to be effective. To increase capacity, the production systems must be duplicated. Current capacities for this approach (approximately 80,000 arrays for 1997) do not meet the needs for the drug discovery market, where a single company may screen over 100,000 samples per year.

Robotic printing systems currently manufacture microarrays in a largely serial fashion. The geometry of the fluid reservoir is often responsible for the limited degree of parallel biosite deposition. This can be explained by illustrating the process needed to produce a microarray. A "micro" array has a small overall dimension, typically smaller than 2 cm by 2 cm. The actual size is determined by the number of array elements and their spacing, with an emphasis on reducing the overall size as much as possible to reduce reagent costs and sample requirements. If a parallel printing approach is implemented using multiple pins or depositiors, the geometries of these depositors must allow them to interface with the probe solution reservoirs and still be able to fit within the confines of the area to be occupied by the microarray. If a 1 cm$^2$ 100 element microarray (10×10) is to be constructed using a standard 384 well microplate with wells spaced 4.5 mm on center as the probe solution reservoir, only 4 depositors can be used to print simultaneously within the microarray. A total of 25 cycles of loading and printing would be required to complete the array. In comparison, this array would be manufactured with a single print step for a capillary bundle printer with 100 capillaries. This is 50 times faster than robotic depositors using a load and dispense technique. If the same array is condensed into a 0.5 cm$^2$ area, then only one depositor can be used, resulting in a 200-fold differential in manufacturing time compared with the capillary bundle printer.

An important feature of the capillary bundle printer is the manner in which it interfaces to the printing solution storage vessel. The capillary bundles have a printing (distal) end and a storage vessel end. The printing solution is held in a sealed container that positions every capillary in the printing bundle via a manifold so that each capillary dips into a specific well (supply chamber) of a microtiter plate, one capillary per well. Current multi-well microtiter plates are available with 96, 384, or 1536 wells, and can contain up to 96, 384, or 1536 individual probe solutions, respectively. For microarrays containing more probe elements, multiple printing solution reservoirs or storage vessels can be interfaced to a single print head, as illustrated in FIG. 4a. This design concept eliminates the geometry problems associated with load and dispense systems. The flexible fused silica capillaries can be gathered together with the array templates or sleeves to create a print head with capillaries spaced as close as 200 μm center to center.

The enclosed printing solution storage vessel is purged with an inert gas during the priming step of the printing process, which also serves to maintain an inert environment for the probe solutions. Contamination of the probe solutions is minimized because of the single direction of flow through the capillaries. The printing end does not dip into the reservoir after every print cycle as in the load and dispense techniques. This is important with contact printing where the depositors touch the surface of the chip or slide that will contain the microarray. These surfaces are chemically treated to interact or bind to the probe solutions. Residual reactive chemicals, or even dust and dirt could be introduced into the probe solution supply chambers with load and dispense systems. Often, the solution to be printed is available in limited quantity or is very expensive. This is often the case in pharmaceutical drug discover applications where small molecule libraries, containing hundreds of thousands of unique chemical structures that have been synthesized or collected and purified from natural sources, are used in high throughput screens of as many potential disease targets as possible. These libraries must be used as efficiently as possible. The amount of fluid that is required for each printing system varies depending on the design. Most require a minimum of 100 microliters (μL) and are able to print less than 1,000 slides, with a significant amount of solution lost to washing between print cycles. The capillary array printer requires only 3 μL with less than 1 μL used for the initial priming. This volume of printing solution is sufficient to print between 20,000 to 30,000 microarrays with each capillary dispensing 50 to 100 pL per array. Load and dispense systems deliver anywhere from 800 pL to several nL per array.

The highly parallel approach allows probe solution deposition in a microarray geometry (less than 2 cm×2 cm) independent of the geometry of the probe solution storage vessel. This permits production of an entire microarray containing from 2 to >10,000 unique capture probes (biosites) in a single stamp of the print head.

The flexible fused silica tubing (or other suitable material such as glass, Teflon or other relatively inert plastic or rubber, or thin, flexible metal, such as stainless steel) originating at the printing storage vessel, pass through a series of arraying templates or sleeves that are held at specific locations in the print head. An attachment site holds the capillaries in a fixed position that does not generally allow horizontal or vertical movement. The capillaries extend down from this anchor point through an open area ("flexation zone") and into a set of array templates or sleeves. These lower array templates or sleeves serve to hold the printing capillaries in a geometry that matches the microarray to be printed. The array templates limit the lateral movement of the printing capillaries to preserve the correct printing pattern, while allowing unrestricted vertical movement of each printing capillary independently of each other. This feature allows the print head to print on slightly irregular or uneven surfaces. The print head moves downward to contact the substrate that is to receive the probe solutions, after the initial contact, the downward movement continues (the distance depends on the surface, from 100 $\mu$m to a few mm) to ensure that all of the printing capillaries contact the surface. The flexation zone positioned between the attachment site (that is holding the capillaries fixed) and the array templates or sleeves allows each capillary to bend so as to accommodate the "overdrive" of the print head. When the print head moves up away from the substrate, the printing capillaries straighten out again.

The capillary bundle originates in an enclosure containing discrete fluid supply chambers, such as the wells in a microtiter plate. Each capillary is inserted into a specific well, which usually contains a unique probe solution with respect to the other wells. The storage vessel can be momentarily pressurized to begin the fluid flow in all of the capillaries simultaneously to prime the printer. After priming, continuous flow of the probe solutions through the capillaries is thereafter facilitated by adjusting the head height $\Delta H$ (the vertical distance from the upper fluid reservoir and the printing tips, as shown in FIG. 4), or by electro-osmotic or electrophoretic force (where the tubes, storage vessels, and reaction chambers are appropriately modified to maintain and modulate an electro-osmotic and/or electrophoretic potential). The chamber can maintain an inert environment by pressurizing the chamber with an inert gas, such as nitrogen or argon.

Fluid volumes deposited at each biosite can be modified by adjusting the head height, by applying pressure to the printing solution storage vessel, by changing the length or inner dimension of the printing capillaries, or by adjusting the surface tension of the probe solution or the substrate that is being printed.

The prime and continuous print with multiple capillaries prevents contamination of the probe solution that can occur with load and dispense systems, which must contact the surface and then return to the probe solution to draw more fluid. The continuous printing of the capillary bundle printer is extremely efficient and proves to be an enabling technique for applications that require the use of small volumes of probe solution. The small outer and inner diameters of the printing capillaries allow for printing as many as 10,000 spots per $\mu$L from a total volume of less than 5 $\mu$L.

In an alternative embodiment, the capillary tubes may be essentially rigid tubes (e.g., stainless steel) mounted in flexible or movable fashion at the attachment site, and slidably held by an array template. In this embodiment, the plurality of capillary tubes can be pressed against a reaction substrate and "even up" at their distal ends by moving lengthwise through the array template, thus accommodating uneven deposition surfaces.

3. Photolithography/Capillary Deposition

To increase the spatial resolution and precision of the capillary deposition approach, a combined photolithographic chemical masking and capillary approach is taught herein. The first photolithographic step selectively activates the precise biosite areas on the reaction substrate. Once selective activation has been achieved, the resulting capillary deposition results in uniform biosite distribution.

Many different substrates can be used for this invention, e.g., glass or plastic substrates. With glass substrates, the procedure begins by coating the surface with an aminosilane to aminate the surface. This amine is then reacted with a UV sensitive protecting group, such as the succimidyl ester of $\alpha$(4,5-dimethoxy-2-nitrobenzyl) referred to as "caged" succimidate. Discrete spots of free amine are revealed on the caged succimidate surface by local irradiation with a UV excitation source (UV laser or mercury arc). This reveals free acid groups which can then react with amine modified oligonucleotide probes. Such a process provides for local biosite modification, surrounded by substrate areas with a relatively high surface tension, unreacted sites.

When using plastic substrates, the procedure begins by coating aminated plastic with an amine blocking group such as a trityl which is poorly water soluble and hence produces a coating with high surface tension. Next, an excitation source (eximer or IR laser for example) is used to selectively remove trityl by light-induced heating. The biosite areas are then activated with bifunctional NHS ester or an equivalent. The net result is similar for glass wherein the locally activated biosite areas will have low aqueous surface tension which are surrounded by relatively high surface tension, thereby constraining the capillary dispensing to the biosite area.

Step 2—Self Assembling Arrays—Universal Arrays

Creating and constructing self assembling probe arrays or universal arrays enables on-line configuration of the biosites wherein an unvarying probe array (capture probes) is activated by binding to a cognate set of adapters (target probes) to yield a modified probe array which is specifically configured for analysis of a target or target mixture.

The Universal Array format overcomes significant obstacles that currently prevent probe array technology from being implemented in a commercially broad manner. Fundamentally, probe arrays that allow for highly parallel analysis of binding events require specialized equipment to manufacture and sophisticated instrumentation to interpret the binding patterns. Unfortunately, the current manufacturing processes for making biosite arrays, such as ink-jet, robotic deposition, or photolithographic in-situ synthesis are relatively inflexible. These techniques are designed to make a large number of specific arrays to cover the cost of setup and operation. Hence, small volume custom arrays would be prohibitively expensive.

Figure 5A:
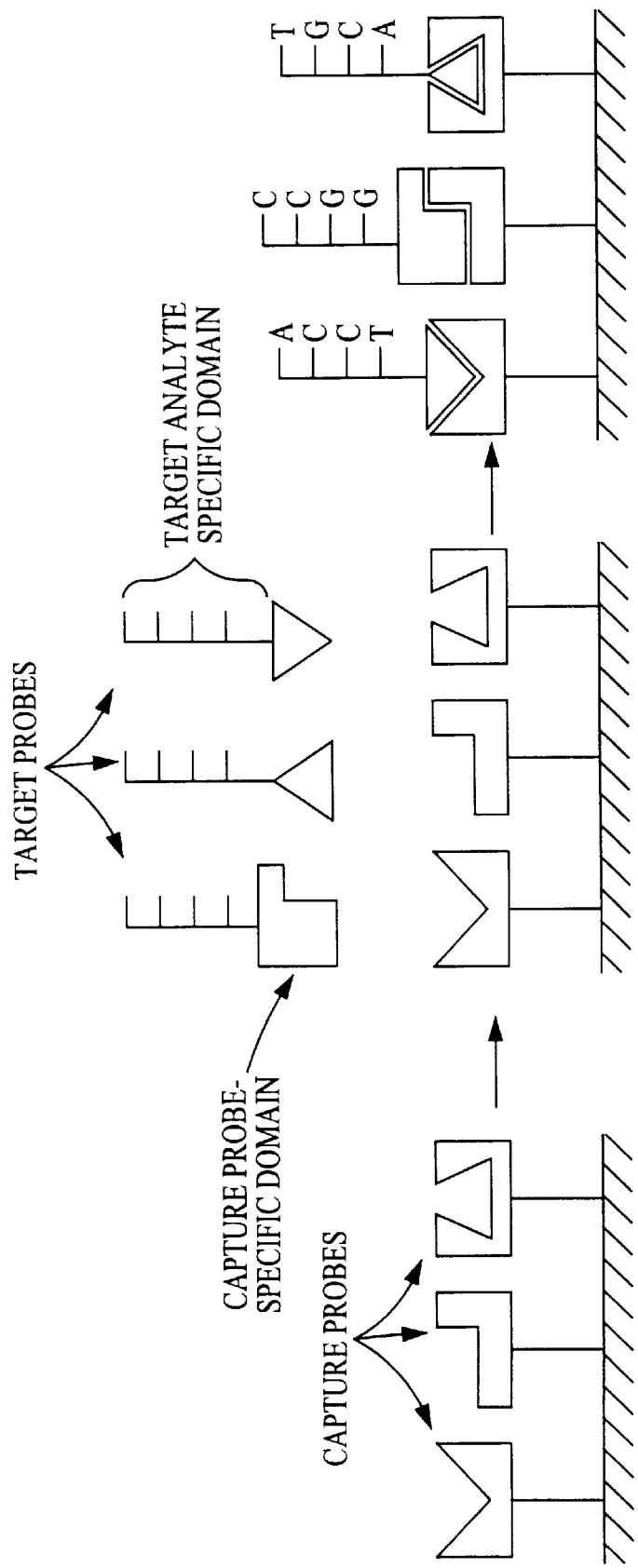
FIG. 5a is a diagram illustrating the Universal Array concept.

In contrast, the Universal Arrays system as taught herein solves this problem by taking advantage of efficient high volume manufacturing techniques for the capture probe arrays only. In this fashion, each customer can use a pre-manufactured, high density biosite capture array that is readily "tailored or customized" by the end-user for their specific target analyte screening. For this invention, "target analyte" is defined as the solution-state solute to be analyzed via binding to the probe array. In short, customization of the array can be performed in the customer's laboratory. The end-user synthesizes or produces bifunctional target probes containing two separate binding domains, one binding domain cognate to a specific member in the array (capture domain) and another binding domain specific for the target analytes of interest (target domain). In an actual assay, end-users add their customized bifunctional probes to a solution phase mixture of analytes and incubate in a reaction chamber containing a pre-manufactured universal capture array. Alternatively, the capture array is incubated first with the bifunctional probes followed by an addition of the analyte mixture (see FIG. 5). FIG. 5a is a diagram showing a Universal Array. The analytes self assemble onto the array in a sandwich-mode by selective binding of their bifunctional probes to both the complementary portions of the target and the capture array. The resulting addressable, self assembled arrays is easily analyzed with the complimentary proximal detector/imager. Teachings for constructing the surface bound capture probes and target probes are outlined below.

1. Capture Probes

The surface bound universal capture probes are arranged in an array of biosites attached to a solid support. Each biosite consists of a multitude of specific molecules distinct in function or composition from those found in every other biosite in the array. These capture probes are designed to have a specific composition or sequence to provide rapid and efficient binding to the capture domain of the target probes. The specific composition is also chosen to minimize cross association between capture probes and their specific target probes.

Specifically for a nucleic acid capture probe the surface bound capture array should be designed for optimum length, base composition, sequence, chemistry, and dissimilarity between probes.

The length of the nucleic acid capture probe should be in the range of 2–30 bases and preferably in the range of 5–25 bases. More preferably, the length ranges from about 10–20 bases and most preferably is at or about 16 bases in length to allow for sufficient dissimilarity among capture probes. Length is also adjusted in this range to increase target probe binding affinity so that capture probe arrays can be activated by addition of target probe mixtures as dilute as $10^{-9}$M. This allows target probes to be synthesized in small scale and inexpensively. Also, length is adjusted to this range to reduce the rate of target probe dissociation from capture probe arrays. This allows the activated capture probe arrays to be washed thoroughly to remove unbound target probes, without dissociation of specifically bound target probes from the surface. With capture probes in such a size range, the complex formed by and between the target probe and capture probe interaction is stable throughout subsequent air drying, and can be stored indefinitely with refrigeration.

A preferred percentage base composition for capture probe array sets is in the range of at or around 30–40% G, 30–40% C, 10–20% A, 10–20% T. Relatively G+C rich capture probes are desirable such that the thermodynamic stability of the resulting capture/target probe pairing will be high, thus allowing for surface activation at low added target probe concentrations (e.g., in the range of $10^{-9}$M). Nearest neighbor frequency in the capture probe set should minimize G-G or C-C nearest neighbors. This criterion minimizes the possibility of side reactions, mediated via G-quartet formation during capture probe attachment to the surface, or during the capture probe-target probe binding step.

For capture probe sets it is desirable to obtain a set structure such that each member of the capture probe set is maximally dissimilar from all others. To obtain such maximally dissimilar sets, the following algorithm can be employed.

1) The set size is defined. In a preferred embodiment, 16, 24, 36, 48, 49, 64, 81, 96 and 100 constitute useful sizes.

2) The overall sequence structure of the capture probe set is defined. The length and base composition as described above are used to define such parameters. In general, the number of G bases and C bases are held equal as are the number of A bases and T bases. This equality optimizes the configurational diversity of the final sets. Thus, such sets will be described by the equation $G_n C_n A_m T_m$.

3) For a set structure defined by m and n, a random number generator is employed to produce a set of random sequence isomers.

4) One member of the random sequence set is selected to be used as element #1 of the set.

5) The maximum similarity allowable among set members is defined. Similarity is defined in terms of local pair-wise base comparison. For example, when two oligomer strands of identical length n are aligned such that 5' and 3' ends are in register, the lack of mismatches refers to the situation where at all positions 1-n, bases in the two strands are identical. Complete mismatching refers to the situation wherein, at all positions 1-n, bases in the two strands are different. For example, a useful maximum similarity might be 10 or more mismatches within a set of 16, 16 mer capture probes.

6) A second member of the random sequence set is selected and its similarity to element #1 is determined. If element #2 possesses less than the maximum allowable similarity to element #1, it will be kept in the set. If element #2 possesses greater than the maximum allowable similarity, it is discarded and a new sequence is chosen for comparison. This process is repeated until a second element has been determined.

7) In a sequential manner, additional members of the random sequence set are chosen which satisfy the dissimilarity constraints with respect to all previously selected elements.

Standard deoxyribonucleic acid base homologues, or homologues with modified purine or pyrimine bases, or modified backbone chemistries such as phophoramidate, methyl phosphonate, or PNA may be employed in synthesis of capture probes.

The capture probe should be linked to a solid support. This can be done by coupling the probe by its 3' or 5' terminus. Attachment can be obtained via synthesis of the capture probe as a 3' or 5' biotinylated derivative, or as a 3'/5' amine modified derivative, a 3'/5' carboxylated derivative, a 3'/5' thiol derivative, or as a chemical equivalent. Such end-modified capture probes are chemically linked to an underlying microtiter substrate, via interaction with a streptaviden film (for biotin), coupling to surface carboxylic acids or epoxide groups or alkyl halides or isothiocyanates (for amines) to epoxides or alkyl halides (for thiols) or to surface amines (for carboxylic acids). Other attachment chemistries readily known to those skilled in the art can be substituted without altering general performance characteristics of the capture probe arrays. Capture probe arrays can be fabricated by such chemistries using either robotic or micro ink jet technology.

In order to minimize cross hybridization during the target probe activation step, capture probe sets are constructed such that every member of the capture probe set has a length which is identical or differs by no more than 1 base from the average length of the set, and possesses an overall gross base composition which is identical or substantially similar to all other members of the set. These two criteria interact to allow the free energy of all target probe/capture probe pairings to be identical. The above described algorithm generates such sets of probes.

It is important that the sequence of each member of the capture probe set differ from every other member of the capture probe set by at least 20%, preferably 40%, more preferably 50% and most preferably 60%. This extent of sequence homology (less than 80% between any two members of the set) prohibits target probes from binding to members of the probe set other than that to which it has been designed.

There are numerous capture probe sets that satisfy the general design criteria as outlined above. Presented below is a specific example of a 16 element capture probe set generated by the above described algorithm which adequately satisfies the above criteria.

For this example, capture probe length is held at 16 bases and base composition is fixed at $G_5C_5T_3A_3$ among all 16 members of the set. There are no more than 3 G-G or C-C pairings per capture probe element. This particular capture probe set is designed to be linked to microtiter support via an amine linkage at its 3' terminus. However, a 5' amine linkage, or other chemistries could have been used as well.

The top-most array element (#1) has been chosen as a standard. Detailed inspection of this set shows that every member of the set differs from every other member of the set by at least 10 base mismatches, thus satisfying the criterion of no more than 50% homology between capture probe set elements.

| SEQUENCE# | CAPTURE PROBES, 16 MERS |
| --- | --- |
| SEQ ID NO:1 | 5'-TGATTCAGACCGGCCG-3'a |
| SEQ ID NO:2 | 5'-CCCGGGGCGTCTTAAC-3'a |
| SEQ ID NO:3 | 5'-GGACGCCATATGCGCT-3'a |
| SEQ ID NO:4 | 5'-TGAGGGCTCCGCCATA-3'a |
| SEQ ID NO:5 | 5'-AACCCGTGACGTGTGC-3'a |
| SEQ ID NO:6 | 5'-AGCATCGCCGGTCCTG-3'a |
| SEQ ID NO:7 | 5'-CCTGCAAGGCTGACGT-3'a |
| SEQ ID NO:8 | 5'-CAGTTGTCGACCCCGG-3'a |
| SEQ ID NO:9 | 5'-CGGCGCGTCCAATTCG-3'a |
| SEQ ID NO:10 | 5'-ATCGATCTGAGGGCCC-3'a |
| SEQ ID NO:11 | 5'-GTACATGCGGCCTGCA-3'a |
| SEQ ID NO:12 | 5'-TAGCCGCTCGCTAGAG-3'a |
| SEQ ID NO:13 | 5'-CCTAGTGATGACCGGC-3'a |
| SEQ ID NO:14 | 5'-GTCTGAGGGCAACCTC-3'a |
| SEQ ID NO:15 | 5'-CTAGCTGGCTACGCAG-3'a |
| SEQ ID NO:16 | 5'-GCCATCCGCTTGGAGC-3'a | a = amine linkage to solid support, such as a 3' propanolamine, coupled to a carboxylate modified surface via amide linkage or epoxide modified surfaces.

| SEQUENCE# | ELEMENTAL TARGET PROBES (cognate to capture probes) |
| --- | --- |
| SEQ ID NO:17 | 3'-TTACTAAGTCTGGCCGGC-5' |
| SEQ ID NO:18 | 3'-TTGGGCCCCGCAGAATTG-5' |
| SEQ ID NO:19 | 3'-TTCCTGCGGTATACGCGA-5' |
| SEQ ID NO:20 | 3'-TTACTCCCGAGGCGGTAT-5' |
| SEQ ID NO:21 | 3'-TTTTGGGCACTGCACACG-5' |
| SEQ ID NO:22 | 3'-TTTCGTAGCGGCCAGGAC-5' |
| SEQ ID NO:23 | 3'-TTGGACGTTCCGACTGCA-5' |
| SEQ ID NO:24 | 3'-TTGTCAACAGCTGGGGCC-5' |
| SEQ ID NO:25 | 3'-TTGCCGCGCAGGTTAAGC-5' |
| SEQ ID NO:26 | 3'-TTTAGCTAGACTCCCGGG-5' |
| SEQ ID NO:27 | 3'-TTCATGTACGCCGGACGT-5' |
| SEQ ID NO:28 | 3'-TTATCGGCGAGCGATCTC-5' |
| SEQ ID NO:29 | 3'-TTGGATCACTACTGGCCG-5' |
| SEQ ID NO:30 | 3'-TTCAGACTCCCGTTGGAG-5' |
| SEQ ID NO:31 | 3'-TTGATCGACCGATGCGTC-5' |
| SEQ ID NO:32 | 3'-TTCGGTAGGCGAACCTCG-5' |

2. Target Probes

A target probe set is designed and constructed to bind to the capture probe set in a specific manner, i.e., each target probe element binds to only one element of the capture probe set. Thus, a mixture of target probes can be administered to a capture probe array formed on the bottom of a microtiter well, or equivalent surface. For the nucleic acid embodiment of the Universal Array, subsequent to binding, the target probe set will partition itself among capture probe set members via Watson-Crick base pairing, thereby delivering a unique binding domain (cognate to analyte) to each site in the probe array.

There are two general methods that can be employed by the end-user to synthesize customized nucleic acid-based bifunctional target probes. The simplest and most direct method is to synthesize a single oligonucleotide that contains the two domains (capture and analyte) separated by a linker region using a standard automated DNA synthesizer. As a class, the bifunctional target probes for a nucleic acid embodiment possess a structural domain cognate to the capture probe which is the Watson-Crick complement to one element of the capture probe set. Its length and base sequence is thus defined by that of the capture probe via standard rules of antiparallel Watson-Crick duplex formation. In addition, the target probe also contains one of the following structural domains:

a. Cognate to a Small Segment of a Solution State Nucleic Acid Target Analyte

This is the component of the target probe which is complementary via Watson-Crick pairing to the solution state target nucleic acid to be analyzed. In general, its sequence has no correlation to that of the domain which is cognate to the capture probe. However, several general design criteria should be met.

First, for ease of target probe synthesis, the unique domain in the range of about 5–30 bases in length, and preferably in the range of about 10–25 bases in length. With shorter target probe domains, analyte binding affinity is insufficient, and longer target probe domains present synthesis difficulties.

Second, when the unique sequence is equal in length or longer than the capture probe set, the unique element should possess a sequence which is no more than 80% homologous to the Watson-Crick complement of any capture probe element. This criterion eliminates inappropriate association of the unique target probe segment with members of the capture probe set.

b. Cognate to a Priming Site Used for Biochemical Amplification Such as PCR and LCR This domain essentially creates nucleic acid amplification primers with tails complementary to capture probe sites in a Universal Array. After amplification, the resulting amplicon sets can be directly hybridized to the capture probe array and analyzed as described below.

C. Chemically Modified for Direct Linkage

Another method of synthesizing bifunctional DNA target probes consists of individually and separately synthesizing analyte and capture sequence oligos that are chemically altered to incorporate a reactive functionality which will allow subsequent chemical linkage of the two domains into a single bifunctional molecule. In general, the 5' or 3' terminus of each oligo is chemically altered to facilitate condensation of the two sequences in a head to tail or tail to tail manner. A number of methods are known to those skilled in the art of nucleic acid synthesis that generate a variety of suitable functionalities for condensation of the two oligos. Preferred functionalities include carboxyl groups, phosphate groups, amino groups, thiol groups, and hydroxyl groups. Further, chemical activation of these functionalities with homo- or heterobifunctional activating reagents allows for condensation of the activated oligo with the second functionalized oligo sequence. Some examples of the various functionalities and activating reagents that lead to condensation are listed below:

| Terminal Functionality (3' or 5') | ACTIVATING AGENT (Homo or Heterobifunctional) |
| --- | --- |
| $NH_2$ (amino) | NHS—NHS, NHS-maleimide, iodoacetic anhydride, EDC (carbo-diimide) |
| $SH_2$ (thiol) | maleimide-NHS |
| COOH (carboxyl) | EDC (carbodiimide) |
| OH (hydroxyl) | carbodiimide (EDC) |
| $PO_4$ (phosphate) | N-methylimidazole (EDC) |
| $PO_3S$ alpha-thiophosphate | maleimide-maleimide, maleimide-NHS |

Figure 5B:
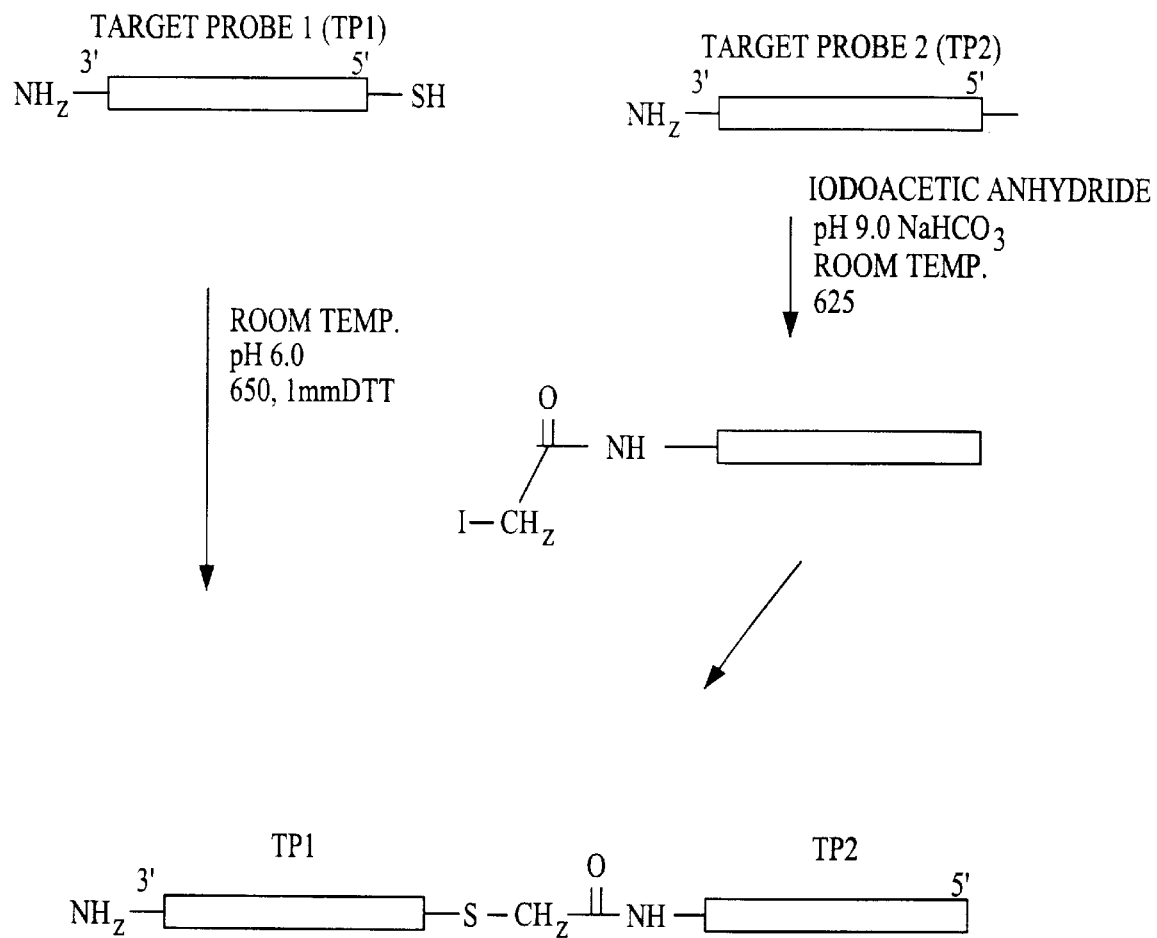
FIG. 5b is a diagram showing direct binding for a target probe associated with the Universal Array.

A specific example of the target probe domains that are cognate to the capture probe set of the Universal Array and can be modified to allow for direct binding to a specifically modified probe, nucleic acid or other molecule capable of selective binding to the analyte of interest is illustrated in FIG. 5b. FIG. 5b is a diagram showing direct binding for a target probe. As shown in FIG. 5b, the target probe is constructed from two parts; the first is a presynthesized probe (TP1) complementary to a capture probe which has a linkage element for attaching the second target complex (TP2). Such embodiment yields a high degree of simplicity for the customer since the first target component can be offered in a ready-to-use format.

A sample protocol for the two piece approach is as follows:

1) Obtain TP1 from commercial source, e.g., Genometrix (synthesized as 3' amine, 5' thiol);
2) TP2 synthesized as an amine;
3) TP2 is mixed with iodoacetic acid anhydride in "Buffer A" to generate the iodoacetate derivative TP2*;
4) Ethanol ppt, run over G25 spin column and collect the excluded volume which contains TP2* only, with small molecule reactants removed;
5) TP1+TP2* are mixed with "Buffer B";
6) Separate on G50 spin column.

For this invention, "Buffer A" consists of 10 mM sodium citrate, pH 7.0, and "Buffer B" consists of 10 mM sodium bicarbonate, pH 9.0.

3. Linker

In some instances, a chemical linker may be needed to separate the two nucleic acid domains of the target probe, to minimize stearic interaction between the target probe and the solution state nucleic acid analyte. This linker may be constructed from nucleic acid building blocks. For example, the sequence $T_n$ (where n=1–5) is preferred because stretches of T are readily synthesized and minimize the likelihood of sequence dependent interactions with capture probe, other target probe domains, or the solution phase nucleic acid analyte.

However, the linker is more preferably synthesized from an inert polymer, such as oligo-ethylene glycolate linkages (—O—CH2—CH2—O—)$_n$. Linkages with n=3 are commercially available as the phosphoramiodate for ready synthesis into oligonucleic acids via standard phosphodiester linkages. From one to five linkers can introduced as needed.

Detailed below is a specific example of the invention based upon the capture probe set described above. Here, the linker domain is listed as two repeats of a triethylene glycolate synthon, linked by a phosphodiester linkage into the target oligonucleotide backbone.

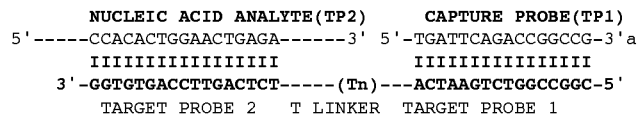

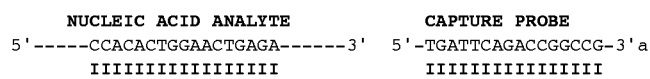

```
                          -continued
       3'-GGTGTGACCTTGACTCT-----(X)-----ACTAAGTCTGGCCGGC-5'
          TARGET PROBE 2    X LINKER    TARGET PROBE 1

X = -OPO2-{O-CH2-CH2-O-OPO2-]2-O DIETHYLENE GLYCOLATE LINKAGE

TARGET PROBE 1
3'AMINE-----------5'-OPO2-O-CH2-CH2-CH2-CH2-CH2-CH2-SH

3' PROPYL AMINE             TARGET PROBE 2
          NH2-CH2-CH(OH)-CH2-OPO2-]2-O-3'-------------5'

IODO ACETATE DERIVATIVE        TARGET PROBE 2
     I-CH2-CO-NH-CH2-CH(OH)-CH2-OPO2-]2-O-3'-------------5'

COUPLED TP1 + TP2 PRODUCT

5' THIOL DERIVATIVE OF TP1     3' ALKYL HALIDE OF TP2

3'-[TP1]-OPO2-O-CH2-CH2-CH2-CH2-CH2-CH2-S-CH2-CO-NH-CH2-CH(OH)-
CH2-OPO2-]2-O-[TP2]-5'

TP1 = target probe 1
TP2 = target probe 2
```

Figure 5C:
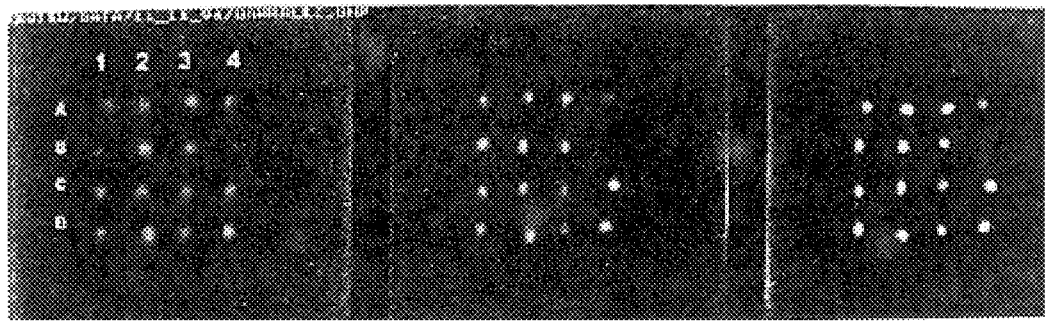
FIG. 5c is a printed computer image showing a multi-microtiter well proximal CCD image of a 4×4 Universal Array.

A Universal Array having 16 capture probes within a single well of a 96 well microtiter plate is shown in FIG. 5c. FIG. 5c is a printed computer image showing a multi-microtiter well proximal CCD image of a 4×4 Universal Array. In FIG. 5c, target specific hybridization is observed in 15 out of the 16 oligo elements in the array. The results of 15 target specific hybridizations conducted simultaneously in 3 separate reaction chambers in a multiwell reaction vessel are quantitatively assessed from the digital image obtained from the proximal CCD imager. Hybrids are digoxigenin end-labeled oligonucleotide targets detected using anti-digoxigenin antibody-alkaline phosphatase conjugate and ELF™ fluorescence. In this assay (from Molecular Probes, Inc.) the antibody binds to the digoxigenin group, delivering alkaline phosphatase to the bound target. The alkaline phosphatase converts the non-fluorescent ELF precursor to a fluorescent product which can be detected by UV irradiation.

Figure 5D:
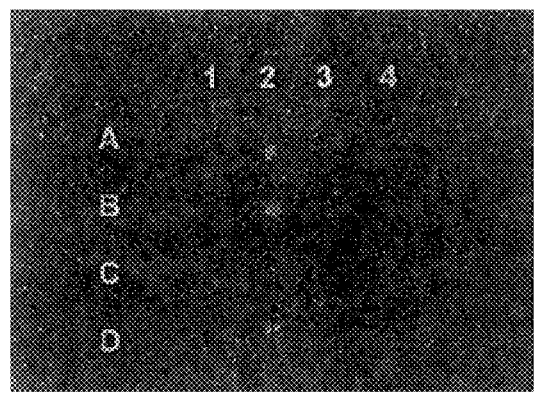
FIG. 5d is a printed computer image showing a single microtiter well proximal CCD image of a 4×4 Universal Array.

FIG. 5d is a printed computer image showing a single microtiter well proximal CCD image of a 4×4 universal array. FIG. 5d shows the target specific hybridization of 4 of the 16 oligonucleotide elements in the array at positions A2, B2, C2, and D2. Note the desirable absence of significant cross hybridization, which has been specifically minimized by imposing the maximum dissimilarly design constraints. Hybrids are digoxigenin end-labeled oligonucleotide targets detected using anti-digoxigenin alkaline phosphatase conjugate and ELF™ fluorescence as described above.

4. Non-Nucleic Acid Embodiments

Small molecule Universal Arrays can be employed for rapid, high throughput drug screening. In this format, surface bound capture probes consist of small haptens or molecules arranged in separated biosites attached to a solid support. Each biosite consists of specifically-addressable, covalently immobilized small molecules such as haptens, drugs and peptides. These organic capture molecules are designed to have a high affinity association with a bispecific ligand. These ligands contains both a domain cognate to the small immobilized organic molecule (capture probe) and cognate to the analyte of interest. The domain cognate to the analyte can associate either directly to this target or to a label on the analyte.

Specific examples of bispecific ligands include, without limitation, antibody:antibody, antibody:receptor, antibody:lectin, receptor:receptor, bispecific antibodies, antibody:enzyme, antibody:streptavidin, and antibody:peptide conjugates.

Analytes can include, but are not limited to, dsDNA, ssDNA, total RNA, mRNA, rRNA, peptides, antibodies, proteins, organic enzyme substrates, drugs, pesticides, insecticides and small organic molecules.

Conversely, the format for a small molecule Universal Array can be inverted so that the macromolecular ligand becomes the capture probe. Thus, a Universal Array (Macromolecular Universal Array) may contain large macromolecules such as, without limitation, antibodies, proteins, polysaccachrides, peptides, or receptors as the immobilized capture probe. In turn, unique small molecule tags having a specific, high affinity association for the macromolecular biosites are covalently attached to various probes cognate to the analyte. These labeled probes now represent the bispecific component cognate to both the capture macromolecule and the target analyte. Some representative examples of small molecules (haptens or drugs) are listed in Table 1 below. This is only a partial list of commercially available antibodies to haptens, steroid hormones and other small molecule drugs. Examples of these bispecific, small molecule-labeled macromolecules include antibodies, receptors, peptides, oligonucleotides, dsDNA, ssDNA, RNA, polysaccharides, streptavidin, or lectins. A partial list of 48 representative compounds for which specific antibodies are available include: fluorescein; dinitrophenol; amphetamine; barbiturate; acetaminophen; acetohexamide; desipramine; lidocaine; digitoxin; chloroquinine; quinine; ritalin; phenobarbital; phenytoin; fentanyl; phencyclidine; methamphetamine; metaniphrine; digoxin; penicillin; tetrahydrocannibinol; tobramycin; nitrazepam; morphine; Texas Red; TRITC; primaquine; progesterone; bendazac; carbamazepine; estradiol; theophylline; methadone; methotrexate; aldosterone; norethisterone; salicylate; warfarin; cortisol; testosterone; nortrptyline; propanolol; estrone; androstenedione; digoxigenin; biotin; thyroxine; and triiodothyronine.

The general concept of Universal Arrays, whether they be DNA-based, small molecule-based, or protein-based allows for great versatility and end-user friendliness. The various configurations described allow for highly parallel, simultaneous, multiplexed, high throughput screening and analysis of a wide variety of analyte mixtures.

Step 3—Molecular Labeling Strategies

Molecular labeling strategies relate to versatile labeling of the target molecules (fluorescence, chemiluminescence, etc.) consistent with proximal large area detection/imaging.

1. Introduction—Conventional Labeling

Labeling can be achieved by one of the many different methods known to those skilled in the art. In general, labeling and detection of nucleic acid hybrids may be divided into two general types: direct and indirect. Direct methods employ either covalent attachment or direct enzymatic incorporation of the signal generating moiety (e.g., isotope, fluorophore, or enzyme) to the DNA probe. Indirect labeling uses a hapten (e.g., biotin or digoxigenin) introduced into the nucleic acid probe (either chemically or enzymatically), followed by detection of the hapten with a secondary reagent such as streptavidin or antibody conjugated to a signal generating moiety (e.g., fluorophore or signal generating enzymes such as alkaline phosphatase or horseradish peroxidase).

For example, methods of detecting the association/hybridization include, without limitation, fluorescent labeling, radioisotope labeling, chemiluminescence labeling, bioluminescence labeling, colorimetric labeling and electrochemiluminescence labeling. Many known labeling techniques require a wash step to remove excess target from the hybridization/association solution, e.g., fluorescent, radioisotope, chemiluminescence, bioluminescence and colorimetric labeling. Several of these will be described below.

2. Fluorescent Labeling

Fluorescent labeling is suitable for this invention for several reasons. First, potentially hazardous substances such as radioisotopes are avoided. Furthermore, the fluorescent labeling procedures are simpler than chemiluminescent methods since the latter requires enzymatic reactions and detection in the solution state. Finally, the fluorescent labeling approach can be modified to achieve the highest signal-to-nose ratio SNR among the safest labeling techniques by utilizing secondary linker chemistries that enable the attachment of hundreds of fluorescent dye molecules per target molecule.

The particular fluorescent dyes to be considered include commercially available agents such as ethidium bromide, as well as the novel dyes proposed in the affiliated chemistry component. These labeling agents have intense absorption bands in the near UV (300–350 nm) range while their principle emission band is in the visible (500–650 nm) range of the spectrum. Hence, these fluorescent labels appear optimal for the proposed proximal CCD detection assay since the quantum efficiency of the device is several orders of magnitude lower at the excitation wavelength (337 nm) than at the fluorescent signal wavelength (545 nm). Therefore, from the perspective of detecting luminescence, the polysilicon CCD gates have the built-in capacity to filter away the contribution of incident light in the UV range, yet are very sensitive to the visible luminescence generated by the proposed fluorescent reporter groups. Such inherently large discrimination against UV excitation enables large SNRs (greater than 100) to be achieved by the CCDs.

3. Electrochemiluminescence Labeling

Figure 6:
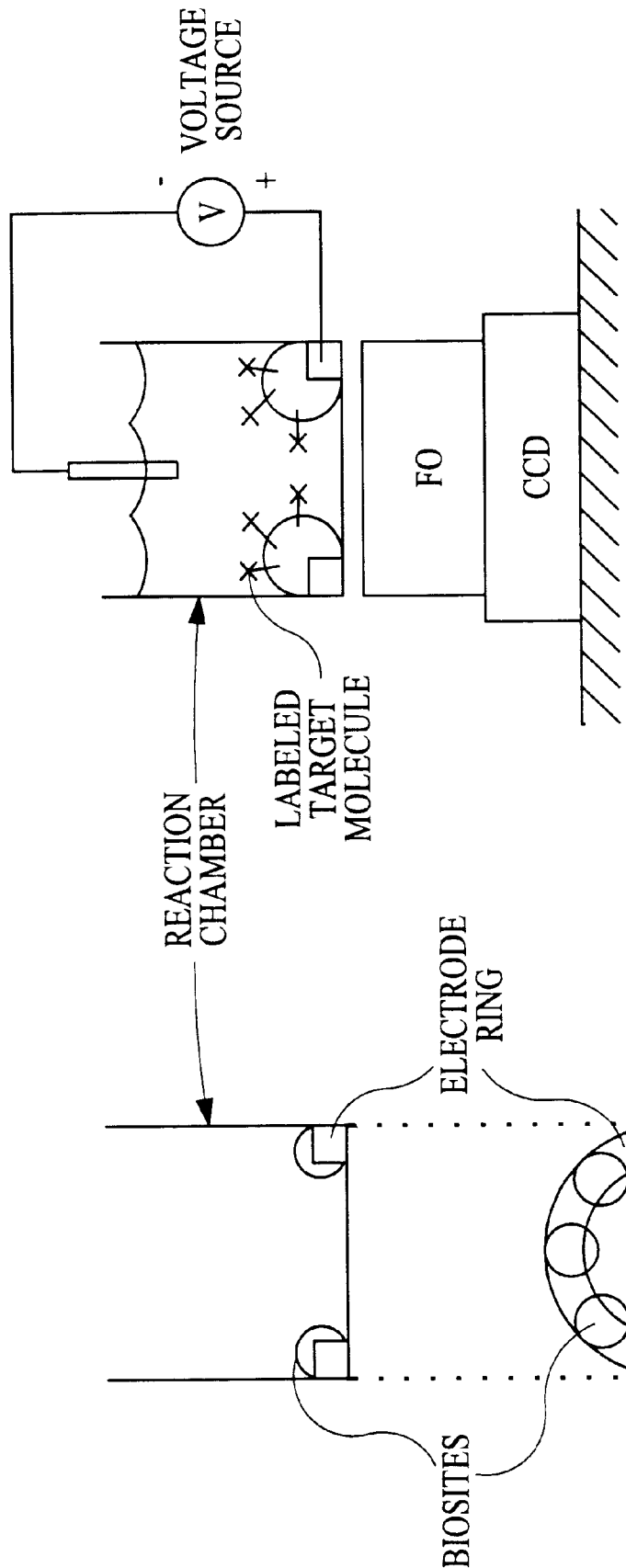
FIG. 6 is a diagram illustrating an ECL implementation in a reaction vessel with proximal CCD imaging.

Electrochemiluminescence or electrical chemiluminescence (ECL) labeling, e.g., ruthenium (Ru) does not require a wash step to remove excess target from the solution and is highly sensitive. Briefly, for electrochemiluminescence as a method of detection, the internal surface of the reaction chamber is coated with a conductive material, e.g., gold, and the biosite is attached to this conductive surface (See FIG. 6). FIG. 6 is a diagram showing ECL implementation in reaction vessel with proximal CCD imaging. Using one microtiter well (of a 96 microtiter well plate) as a reaction chamber, the biosites are deposited onto the internal circumference of the microtiter well by one of several methods as described above (ink-jet, capillary, or photolithography/capillary).

This conductive surface acts as a cathode (positive lead), and an anode (negative lead) is provided by inserting a metal cup with an electrode protruding through its center into the reaction chamber (microtiter well). The electrode is positioned such that it is inserted into the hybridization solution. The voltage applied to the anode induces an electrochemical event at the labeled molecule surface which releases energy in the form of photons (light).

The specific ECL label, e.g., Ru, is attached to the target molecule by the conventional means. The labeled target is added to the hybridization solution and once hybridization occurs between the Ru labeled target and biosite, e.g., after sufficient time has passed for hybridization to be completed, a voltage is applied and only Ru labeled target associated (hybridized) with the biosite will emit light and be detected. In order for the Ru labeled target to be detected, it must be in proximity to the cathode. The residual excess Ru labeled target not associated with the biosite will therefore not emit light.

Figure 7:
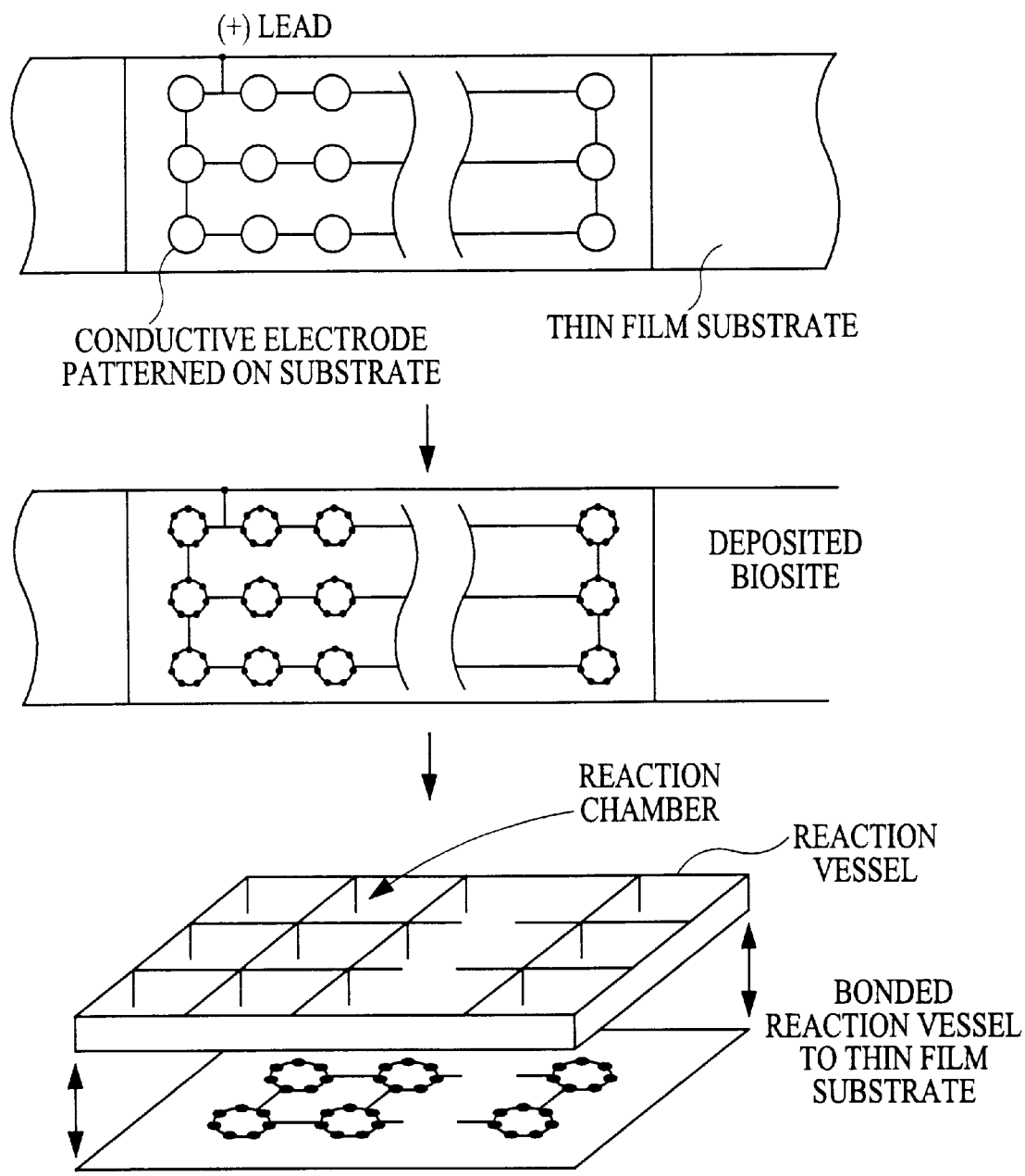
FIG. 7 is a diagram showing fabrication of ECL reaction vessels.

The ECL reaction vessel is diagramed in FIG. 7. In FIG. 7, the thin film substrate, e.g, plastic, glass, etc., is patterned with a conductive metal, e.g., gold, platinum, etc., to form electrodes within the reaction chambers. Next, the biosites are deposited with one of several methods described above (ink-jet, capillary, photolithographic/capillary) onto the patterned electrodes. Finally, the resulting thin film substrate is bonded onto the reaction vessel which serves as the bottom of the reaction chambers.

4. Lanthanide Chelate Labeling

As an alternative to ethidium-based fluorescent reporter groups, which are known for their tendency to absorb nonspecifically to surfaces causing increased signal background, the use of aromatic lanthanide (Ln) chelators may be used in the instant invention. Although the lanthanide ions (Tb and Eu specifically) have luminescent yields near to one (1), and emission lifetimes year to 100 $\mu$sec, they absorb light weakly and are therefore poor luminescent dyes. However, when chelated by an appropriately chosen aromatic donor, energy transfer can occur resulting in high overall luminescent yields. DPA (dipiccolimic acid) is the prototype for such an aromatic Ln chelator, and has excellent photophysical properties. However, its absorbence maximum is near 260 nm, which overlaps the DNA absorption band and is therefore inappropriate for the proximal CCD approach. Thus, the synthesis of modified DPA derivatives with the correct absorption properties and which have the capacity to be linked directly or indirectly to the target molecules have been developed.

Since three DPA equivalents bind per Ln ion, the preferred approach is to link the modified DPA to a polymeric lattice, which provides for close spacing of chelators and can be designed to have useful DNA or RNA binding properties. These results suggest that a fused bicyclic DPA derivative is the candidate of choice.

Figure 8:
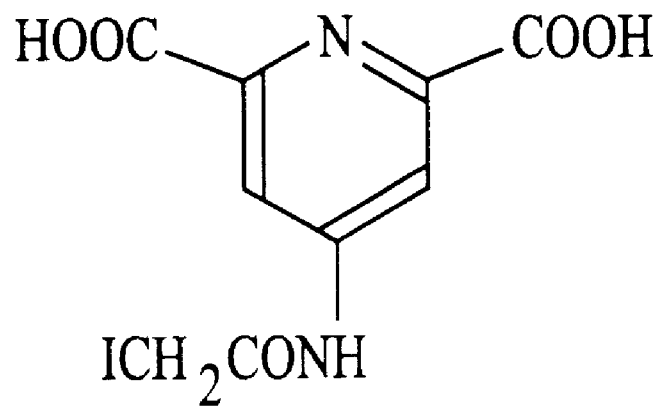
FIG. 8 is a chemical drawing showing lanthanide chelators.
Figure 8:
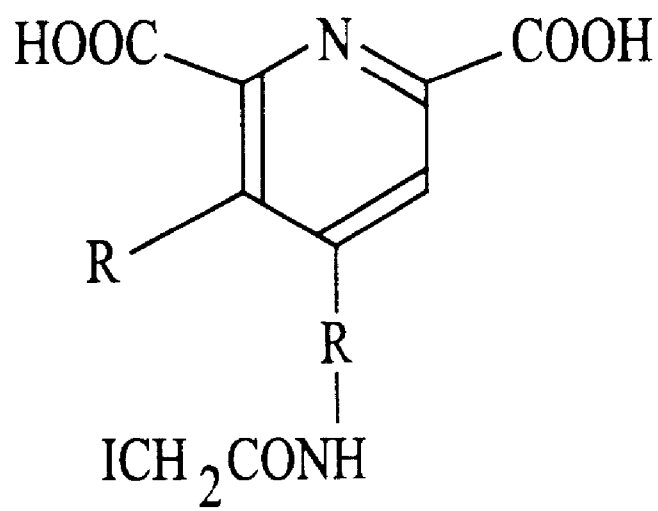

FIG. 8 is a chemical drawing showing lanthanide chelators. The two classes of polymeric latice as illustrated in FIG. 8 can be employed for attachment of DPA derivatives, both based upon the use of synthetic polypeptides in the $10^4$ MW range. Synthesis can be conducted as described for simple DPA-peptide conjugates. The first polymer is to be used for covalent attachment to RNA via the transamination reaction to cytosine. This peptide lattice can be simple poly-L-lys. The second approach involves the coupling of modified DPA to a DNA binding peptide, which can be used to deliver the Ln chelate to RNA by means of non-covalent nucleic acid binding. For example, peptides can be synthesized in solution as a $Lys_3Arg_1$ random co-polymer (average mw $10^4$). Subsequent to the conversion of Lys residues to the modified DPA conjugate, RNA binding can be driven by association with multiple Arg equivalents, taking advantage of the known helix selectivity of polyarginine. As for ethidium bromide (EB), addition of the non-covalent chelator conjugate can be made after washing to retain hybridization stringency.

Step 4—Detection System

A detection system relates to parallel detection and/or imaging in the reaction vessel containing the reaction chambers using a proximal large area detector/imager.

1. General Description

Following the hybridization process of the multiplexed molecular analysis system, the amount of hybridized target molecules bound to each biosite in the reaction chambers of the reaction vessel must be quantitatively determined. The preferred detection/imaging system for quantifying hybridization for the instant invention is proximal charge-coupled device (CCD) detection/imaging due to the inherent versatility (accommodates chemiluminescence, fluorescent and radioisotope target molecule reporter groups), high throughput, and high sensitivity as further detailed below.

The detection/imaging apparatus used for the multiplexed molecular analysis system is comprised of a lensless imaging array comprising a plurality of solid state imaging devices, such as an array of CCDs, photoconductor-on-MOS arrays, photoconductor-on-CMOS arrays, charge injection devices (CIDs), photoconductor on thin-film transistor arrays, amorphous silicon sensors, photodiode arrays, or the like. The array is disposed in proximity to the sample (target molecules hybridized to the biosites) and is comparable in size to the reaction chambers. In this manner, a relatively large format digital image of the spatial distribution of the bound target molecules is produced without requiring the use of one or more lenses between the sample and the imaging array. This apparatus offers:

1) high sensitivity (subattomole DNA detection);
2) high throughput (seconds for complete image acquisition);
3) linear response over a wide dynamic range (3 to 5 orders of magnitude);
4) low noise;
5) high quantum efficiency; and
6) fast data acquisition.

Moreover by placing the imaging array in proximity to the sample as illustrated in FIG. 1, the collection efficiency is improved by a factor of at least ten (100 over any lens-based technique such as found in conventional CCD cameras). Thus, the sample (emitter or absorber) is in near contact with the detector (imaging array), thereby eliminating conventional imaging optics such as lenses and mirrors. This apparatus can be used for detecting and quantitatively imaging radioisotope, fluorescent, and chemiluminescent labeled molecules, since a lensless CCD array apparatus is highly sensitive to both photons and x-ray particles. Hence a single imaging instrument can be used in conjunction with numerous molecular labeling techniques, ranging from radioisotopes to fluorescent dyes.

The detection/imaging apparatus invention as taught herein can be divided into two subclasses. The first subclass entails a static platform, whereby a plurality of imaging devices are arranged in a relatively large format area comparable to the sample size.

The second subclass entails a dynamic platform that enables a smaller set of imaging devices to image a relatively large format sample by moving either the array of imaging devices or sample, relative to one another.

Thus, the dynamic embodiment of the detection/imager invention generally concerns a method and apparatus for ultrasensitive detection, high resolution quantitative digital imaging and spectroscopy of the spatial and/or temporal distribution of particle emissions or absorption from/by a sample (target molecules) in a relatively large format. The apparatus of this invention includes:

a) a large area detector array for producing a relatively large image of detected particle distribution without the use of optical lenses;

b) a scanner for moving either the sensor array or the sample in a manner for efficient imaging; and c) a source of energy for exciting the sample or providing absorption by the sample.

Optimally, the ratio of detector array size to sample image is one (1) for a static format and less than one (1) for a dynamic format.

Figure 9:
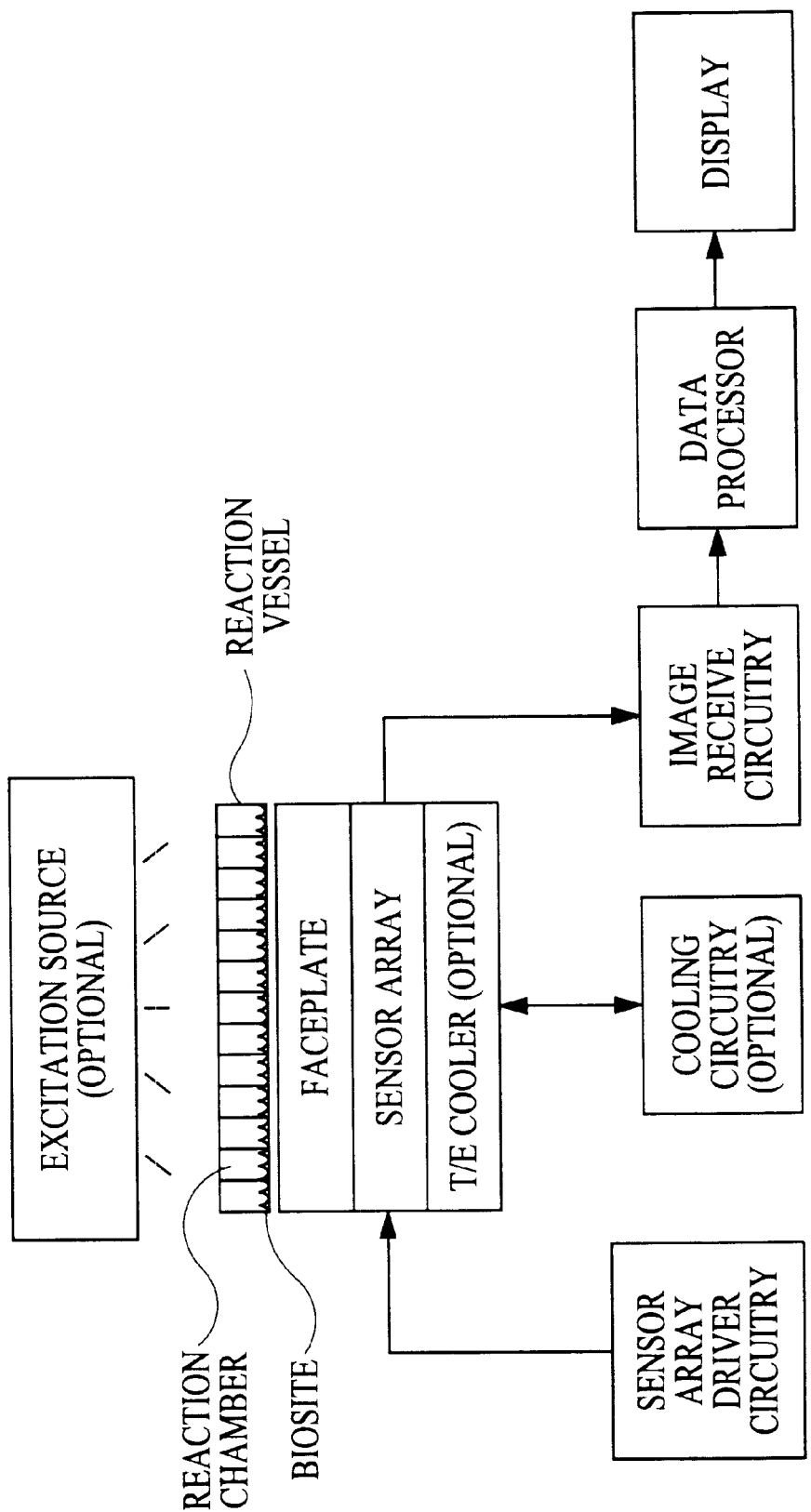
FIG. 9 is a diagram showing the electronics schematic of a multiplexed molecular analysis system.

An electronic schematic of the proximal detector/imager to be used with the multiplexed molecular analysis system is shown in FIG. 9. FIG. 9 is a diagram showing a multiplexed molecular analysis system electronics schematic. As illustrated in FIG. 9, the reaction vessel is placed directly on the fiber optic faceplate which is bonded to the sensor array. The faceplate provides sensor isolation to accommodate routine cleaning, as well as affording thermal isolation for ultrasensitive detection under cooled sensor operation. Also the optical faceplate can serve to filter excitation radiation by employing selective coatings. The sensor array is comprised of a plurality of smaller sensors such that the composite array approaches the surface area of the reaction vessel. The excitation source serves to excite the fluorescent reporter groups attached to the target molecules. Depending on the chosen reporter groups, the excitation source can be either a UV lamp, laser, or other commonly used light source used by those skilled in the art. The sensor array driver circuitry includes clocking, biasing and gating the pixel electrodes within the sensors. The cooling circuitry controls the thermoelectric cooler beneath the sensor array to enable ultrasensitive detection by providing very low thermal noise. Basically, the user selects the required temperature of operation and through feedback circuitry, the sensor array is held constant at such temperature. The image receive circuitry is responsible for obtaining the digital image from the sensor array and includes preamplification, amplification, analog to digital conversion, filtering, multiplexing, sampling and holding, and frame grabbing functions. Finally, the data processor processes the quantitative imaging data to provide the required parameters for the molecular analysis outcome. Also, a computer display is included for displaying the digital image.

2. Sensor Array Implementations

Figure 10A:
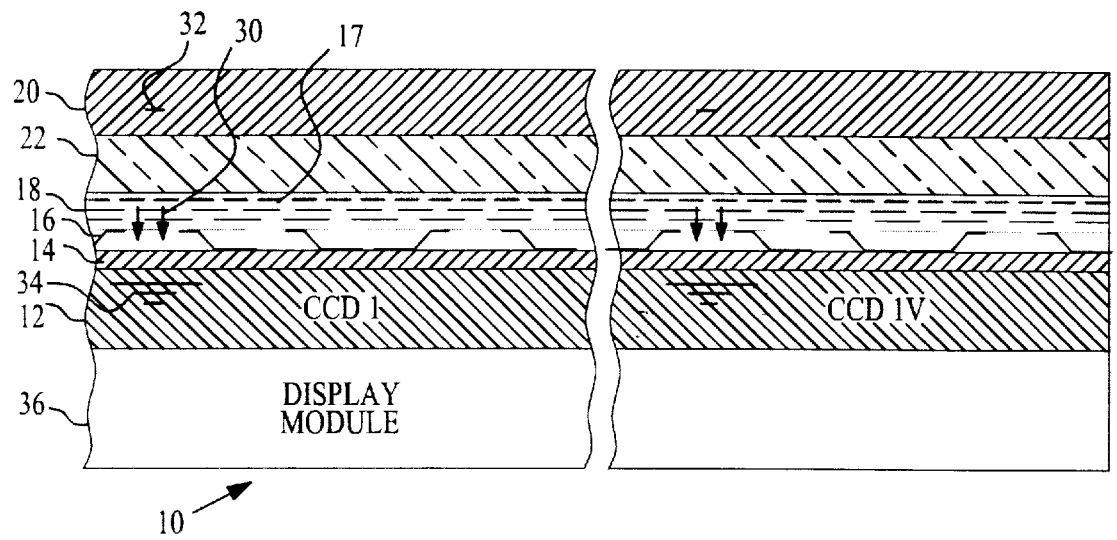
FIG. 10a is a diagram showing a CCD sensor array for the proximal CCD imager.
Figure 10B:
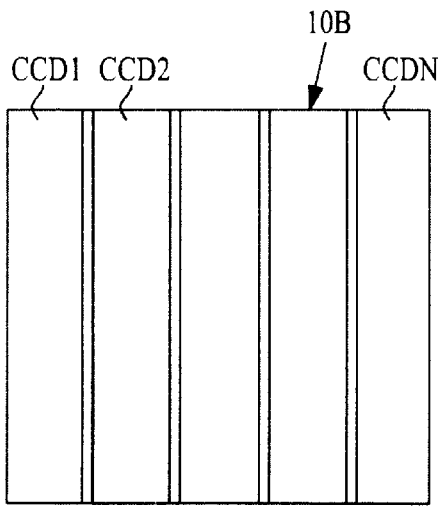
FIG. 10b is a diagram showing the tiling of CCD sensors to form a large format proximal CCD imager.
Figure 10C:
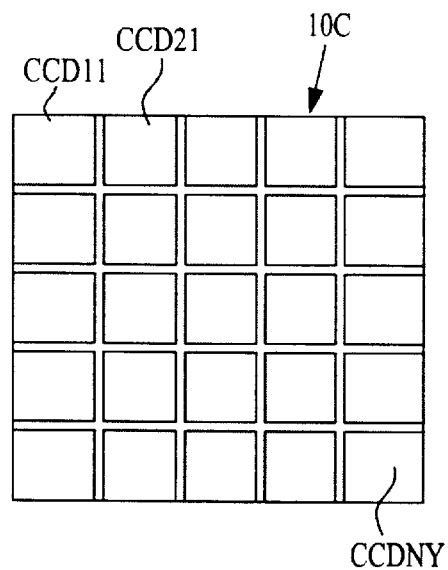
FIG. 10c is a diagram showing an alternative tiling scheme of multiple CCD sensors used to form a large format proximal CCD imager.

A preferred embodiment of the detection/imaging sensor array of the invention consists of a plurality of CCD arrays CCD1 . . . CCDN assembled in a large format module as illustrated in FIGS. 10A–10C. FIG. 10A depicts a CCD array with multiple pixels being exposed to a labeled biological sample 32 which causes the collection of electrons 34 beneath the respective pixel gate 16. Individual CCD arrays are closely aligned and interconnected in particular geometries to form a relatively large (greater than 1 $cm^2$) format imaging sensors of the linear array type as shown in FIG. 10B or the two dimensional row and column type as shown in FIG. 10C.

Numerous CCD tiling strategies can be explored to determine the best tradeoff analysis between detection throughput and instrument cost. A large format tiled array with several wafer scale CCDs would provide simultaneous detection of all biosites within the reaction vessel within seconds. However the cost of the large (8.5×12.2 cm) CCD sensor array may be prohibitive. An engineering compromise is therefore preferred, balancing the use of smaller devices to significantly reduce the cost of the tiled array, while also matching the throughput with the other processes in the overall multiplexed molecular analysis system.

As shown in FIG. 10A, each CCD array CCD1 . . . CCDN is formed, in the conventional manner, by growing and patterning various oxide layers 14 on a Si wafer/ substrate 12. CCD gate electrodes 10 are then formed by deposition of polysilicon or other transparent gate material on the gate insulator or field oxide 14. A dielectric or polymer layer 18, preferably of light transmissive material such as silicon nitride or glass, $SiO_2$ or polyamide is then formed over the electrodes 16.

Preferably, in a labeled molecule embodiment, a filter shown in dotted lines 17, which may be formed of an aluminum or tungsten metal grating, or dielectric multilayer interference filter, or absorption filter, is formed in the dielectric layer 18 between the surface and the metal electrode 16. The filter is adapted to block the excitation radiation and pass the secondary emission from the sample 20. In a static platform embodiment, the sensor module remains fixed with respect to the sample. Hence to achieve the relatively large imaging format, a plurality of imaging devices CCD1 . . . CCDN should be arranged in a module as illustrated in FIGS. 10B and 10C. The module can be packaged for easy installation to facilitate multiple modules, each for specific applications. Various tiling strategies have been documented and can be employed to minimize the discontinuity between devices, such as described in Burke, et al., "An Abuttable CCD Imager for Visible and X-Ray Focal Plane Arrays," *IEEE Trans On Electron Devices*, 38(5):1069 (May, 1991).

As illustrated in FIG. 10A, a reaction vessel 20 is placed in proximity to the CCD array sensor 10. The sample can be excited by an external energy source or can be internally labeled with radioisotopes emitting energetic particles or radiation, or photons may be emitted by the sample when labeled with fluorescent and chemiluminescent substances. Conversely, direct absorption may be used to determine their presence. In this case, the absence of illuminating radiation on the detector may constitute the presence of a particular molecule structure. Preferably the sample can be physically separated from the CCD detector by the faceplate which is transparent to the particle emission.

The CCD detection and imaging arrays CCD1 . . . CCDN generate electron-hole pairs in the silicon 12 (see FIG. 10A) when the charged particles or radiation of energy hv shown by the asterisk 32 arising from or transmitted by the sample are incident (arrows 30) on the CCD gates 16. Alternatively, the CCDs can be constructed in a back illumination format whereby the charged particles are incident in the bulk silicon 12 for increased sensitivity. The liberated photoelectrons 34 are then collected beneath adjacent CCD gates 16 and sequentially read out on a display conventionally.

Silicon based CCDs are preferred as the solid state detection and imaging sensor primarily due to the high sensitivity of the devices over a wide wavelength range of from 1 to 10,000 Å wavelengths. That is, silicon is very responsive to electromagnetic radiation from the visible spectrum to soft x-rays. Specifically for silicon, only 1.1 eV of energy is required to generate an electron-hole pair in the 3,000 to 11,000 Å wavelength range. Thus for visible light, a single photon incident on the CCD gate 16 will result in a single electron charge packet beneath the gate, whereas for soft x-rays, a single beta particle (typically KeV to MeV range) will generate thousands to tens of thousands of electrons. Hence the silicon CCD device provides ultrasensitive detection and imaging for low energy alpha or beta emitting isotopes ($^3H$, $^{14}C$, $^{35}S$) as well as high energy alpha or beta emitting isotopes ($^{32}P$, $^{125}I$). Consequently, the CCD is both a visible imager (applicable to fluorescent and chemiluminescent labeled molecular samples) and a particle spectrometer (applicable to radioisotope labeled samples as well as external x-ray radiated samples). Thus, the CCD can provide simultaneous imaging and spectroscopy in the same image.

In addition to the high sensitivity, the CCDs offer a wide dynamic range (up to 5 orders of magnitude) since the charge packet collected beneath each pixel or gate 16 can range from a few to a million electrons. Furthermore, the detection response is linear over the wide dynamic range which facilitates the spectroscopy function, since the amount of charge collected is directly proportional to the incident photon energy. Hence, no reciprocity breakdown occurs in CCDs, a well-known limitation in photographic film.

3. Scanning Mechanics

To image the reaction vessels with a smaller sized and less expensive sensor array, the reaction vessel can be imaged in a column-by-column manner as it is moved across the sensor array with a scanning mechanism. A plurality of imaging devices can be arranged in a module of columns to minimize discontinuity. Also, the scanning can be accomplished with intentional overlapping to provide continuous high resolution imaging across the entire large format sample area.

EXAMPLE I

DIFFERENTIAL DETECTION OF THREE NHS-IMMOBILIZED HAPTENS USING UNIVERSAL ARRAYS

Figure 18:
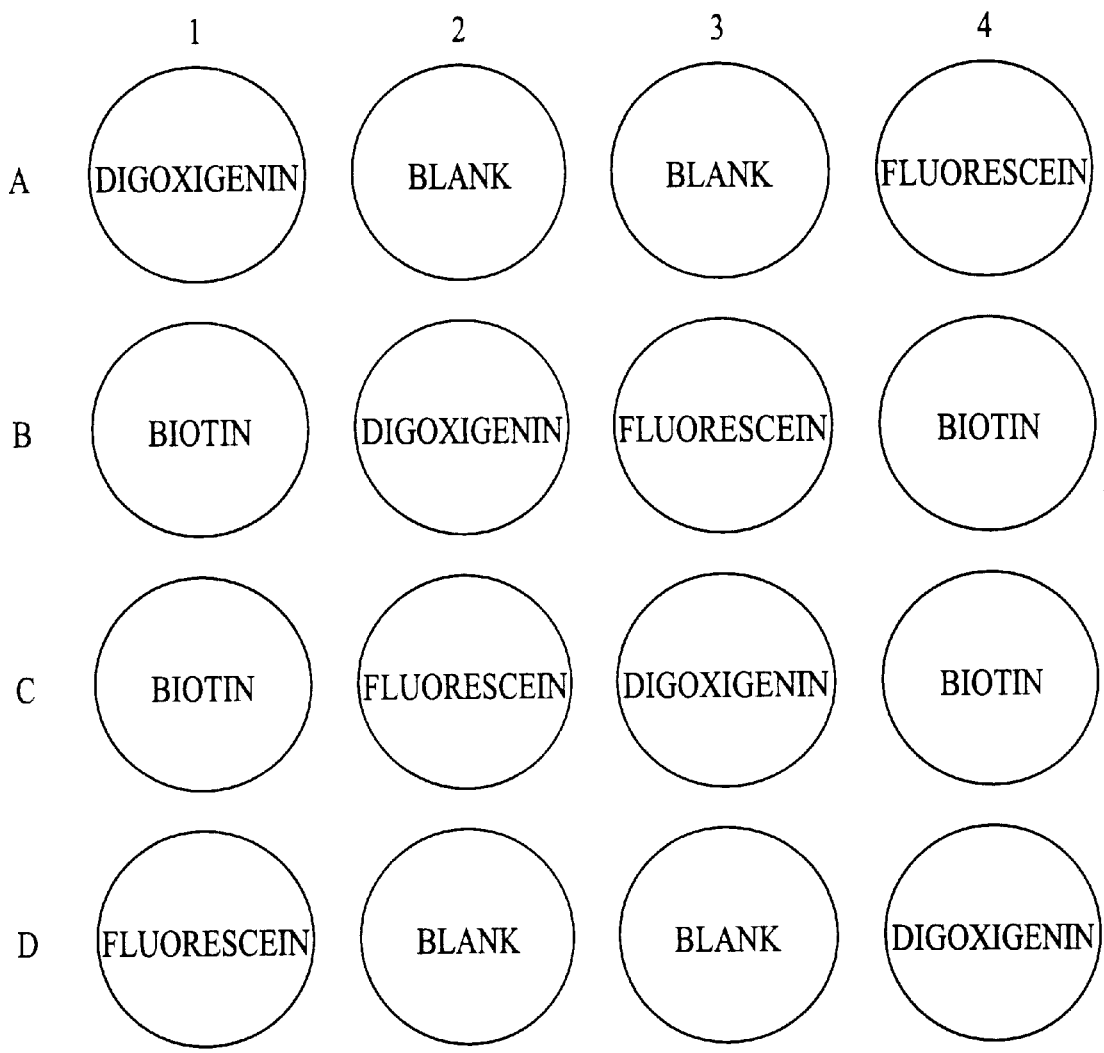
FIG. 18 is a diagram illustrating spatial addresses of small molecules covalently immobilized on amino-derivitized thin-bottom, glass microtiter wells.

This example demonstrates reduction to practice of small molecule universal arrays as illustrated in FIGS. 18 and 19. FIG. 18 is a graphical schematic layout of a microarray that will be printed on glass slides using the Hamilton 2200 Microlab robot. This schematic layout illustrates the relative spatial location/addresses of three separate covalently immobilized haptens on to the glass substrate (e.g., digoxigenin, fluorescein, and biotin). The robot will print the array by depositing 10 nL volumes of each activated hapten (N-hydroxysuccinimide activated) on to an amino-silanized glass surface thus cerating a 4×4 matrix microarray. Each hapten will be deposited by the robot 4 times as illustrated by the schematic. For example, digoxigenin will be deposited at array addresses indicated by address locations A1, B2, C3, and D4. Similarly, fluorescin can be found at address locations A4, B3, C2, and D1 and biotin at B2, B3, B4, and C3 as illustrated in the schematic. A buffer blank (control) will be deposited at locations A2, A3, D2, and D3. These buffer blanks should not generate a signal on the CCD proximal detector in the presence of hapten detecting conjugates.

Incubation of these covalently immobilized hapten microarrays with an appropriate bispecific molecule (e.g., hapten recognition site and enzyme reporter site) such as an antibody/enzyme conjugate and subsequent detection of the appropriate chemiluminescent substrate should generate an image "pattern" on the CCD detector as predicted by the schematic addresses shown in FIG. 18. In this example, specific light generating substrate molecules are localized at predictable/addressable biosites in the array either individually or in a multiplexed fashion.

Briefly, in order to covalently immobilize the above described hapten microarray the following protocol was developed. First, several 22×22 mm square glass microscope cover slides (150 μm thick) were washed in a container containing ALCONOX detergent solution, and subsequently transferred to a clean container containing warm tap water to rinse off the detergent. This rinse step was followed by two separate brief rinses, first in a container containing 100% acetone, then the slides were transferred to a rinse in a solution of 100% methanol. The slides were rinsed one final time in deionized $H_2O$ to remove traces of organic solvent. The clean glass slides were then oven dried at 37° C. After drying, the clean slides were then surface derivitized by vacuum deposition of a solution of 3-aminopropyltrimethoxysilane in a vacuum oven. The slides were laid down in a metal tray on clean lint free paper towels. A 1:3 solution of 3-aminopropyltrimethoxysilane and xylene was freshly prepared by mixing 1 ml of 3-aminopropyltrimethoxysilane (Aldrich) with 3 ml of dry p-xylene solvent in a small glass petri dish. The dish was covered with aluminum foil and a small needle puncture was made in the foil. This solution was placed in the tray with the glass slides. The tray was subsequently covered with aluminum foil and placed in a NAPCO vacuum oven at 75° C. under 25" of Hg vacuum overnight. The next day the amino-silanized glass slides were removed from the vacuum oven and stored in a dry place until used.

In order to robotically dispense and print hapten microarrays, four separate activated hapten solutions were made as follows. First, approximately 1 mg of the following compounds were weighed out into separate weigh boats: fluorescein-5-(and-6)-carbixamido)hexanoic acid, succinimidyl ester, followed by 1 mg of sulfosuccinimidyl 6-(biotinamido) hexanoate and then 1 mg of digoxigenin-3-O-methylcarbonyl-γ-aminocaproic acid-N-hydroxysuccinimide ester. Each activated hapten was dissolved in 100 μL DMSO. Subsequently 50 ul of each hapten was mixed into separate tubes containing 950 ul of 0.1 M $Na_2HCO_3/NaCO_3$ buffer at pH 8.05. A blank solution containing 50 μL of DMSO into this buffer was also made as a control for dispensing on to the array as described above. Each of the four solutions (100 μL) was placed into 16 wells of a microtiter plate. The microtiter plate was then placed on the Hamilton 2200 Microlab robot and 10 nL aliquots were collected and dispensed by the robotic dispensing needle onto the amino-silanized glass cover slides at known address locations illustrated by the schematic layout in FIG. 18.

Following microfluid dispensing of four separate (identical) glass cover slides by the computer controlled robot needle the arrays were air dried for 15 minutes. To detect the immobilized haptens the glass slides were rinsed for 10 minutes in 10 ml of 1×TBS+0.1% Tween® 20 (Tris-Buffered Saline, 100 mM Tris-HCl, 150 mM NaCl, pH 7.5). Individual slides were then incubated with appropriate conjugate dilutions. Image A was generated by incubating one of the slides in 10 ml of a 1:5000 dilution of streptavidin: horseradish peroxidase conjugate in 1×TBS+0.1% Tween® 20. Image B was generated by incubating one of the slides in a 1:5000 dilution of anti-digoxigenin: horseradish peroxidase conjugate. Image C was generated by incubating in a 1:1000 dilution of antifluorescin:horseradish peroxidase conjugate. Finally, Image D was generated by incubating a fourth slide simultaneously with all three horseradish peroxidase conjugates at the above dilutions. Following conjugate incubation all slides were washed by a 10 minute rinse on a platform shaker in 10 ml 1×TBS+0.1% Tween® 20 to remove excess conjugates. The slides were then imaged by adding 200 μL of freshly made chemiluminescent substrate (SuperSignal™ Substrate from Pierce Chemical) as recommended by the manufacturer. The slides containing substrate were imaged by a 10 second integration time at room temperature on the proximal CCD detector described above.

Figure 19A:
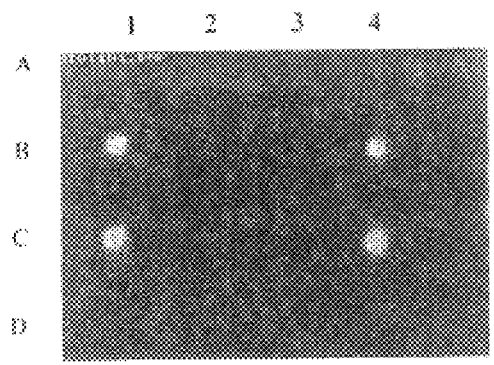
FIG. 19A is a printed computer image showing specific imaging of biotin-addressable biosites detected using streptavidin:HRP conjugate (4×4 single well microarray).

FIG. 19A is a printed computer image showing specific imaging of biotin-addressable biosites detected using streptavidin:HRP conjugate (4×4 single well microarray). In FIG. 19A, Image A was generated by incubating the small molecule 4×4 universal array with a streptavidin:HRP conjugate specific for biotin. As seen in this image, only biosites with addresses B1, C1, B4, and C4 known to contain biotin (refer to FIG. 18) are detected using proximal CCD imaging of chemiluminescent signals. Specific addressing of these biosites generates a "box" image pattern.

Figure 19B:
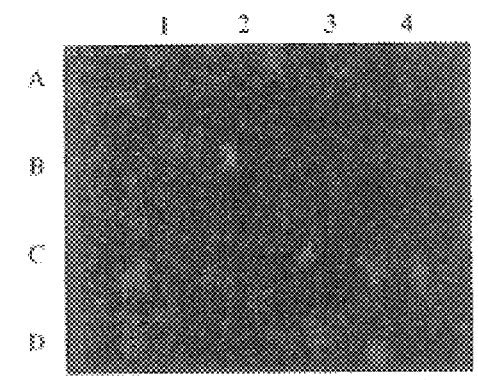
FIG. 19B is a printed computer image showing specific imaging of digoxigenin-addressable biosites detected using anti-digoxigenin:HRP conjugate (4×4 single well microarray).
Figure 19C:
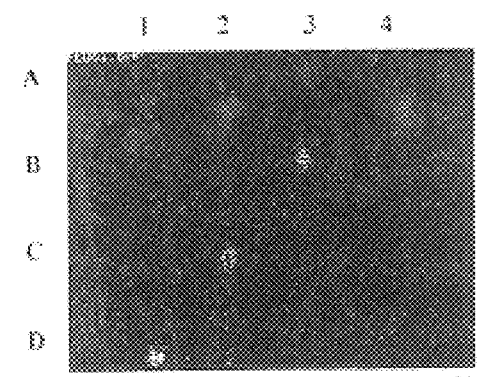
FIG. 19C is a printed computer image showing specific imaging of fluorescein-addressable biosites detected using anti-fluorescein:HRP conjugate (4×4 single well microarray).

As shown in FIGS. 19B and 19C, Image B and Image C are two additional 4×4 microarrays incubated with the indicated antibody conjugate. FIG. 19B is a printed computer image showing specific imaging of digoxigenin-addressable biosites detected using anti-digoxigenin:HRP conjugate (4×4 single well microarray). As seen in 19B, only biosites with addresses A1, B2, C3, and D4 known to contain digoxigenin (refer to FIG. 18) are detected using proximal CCD imaging of chemiluminescent signals. FIG. 19C is a printed computer image showing specific imaging of fluorescein-addressable biosites detected using anti-fluorescein:HRP conjugate (4×4 single well microarray). As seen in 19C, only biosites with addresses A4, B3, C2, and D1 known to contain fluorescein (refer to FIG. 18) are detected using proximal CCD imaging of chemiluminescent signals. Thus, the signals from these two small molecules generate the predicted "diagonals" as illustrated in FIG. 18.

Figure 19D:
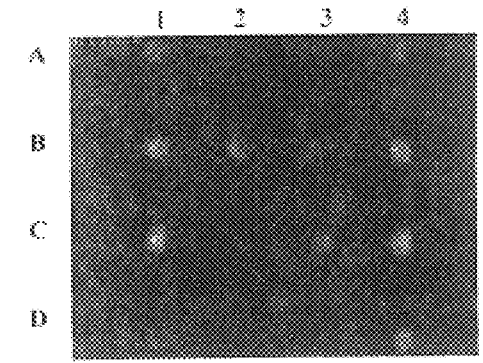
FIG. 19D is a printed computer image showing simultaneous imaging of fluorescein, biotin, and digoxigenin biosites detected using anti-fluorescein, anti-digoxigenin and streptavidin:HRP conjugates (4×4 single well microarray).

Additionally, in FIG. 19D, Image D illustrates simultaneous detection of all three haptens in a single well by simultaneously incubating a single 4×4 array with all three conjugates. FIG. 19D is a printed computer image showing simultaneous imagings of fluorescein, biotin, and digoxigenin biosites detected using anti-fluorescein, anti-digoxigenin and streptavidin:HRP conjugates (4×4 single well microarray). This image generates the predicted "H" pattern as expected because wells A2, A3, D2 and D3 were blank (see FIG. 18).

EXAMPLE II

USE—MICROARRAYS IN A MICROPLATE

Several applications of the multiplexed molecular analysis system are detailed below which can be accommodated with a multiple well microplate serving as the particular reaction vessel. The novelty, however, is the plurality of biosites within each well. That is, each well in the multiple well microtiter plate contains N biosites where N ranges from 2 through 1,000. The upper bound is based on the resolution limitations posed by the bottom substrate of the microtiter plate used in conjunction with the proximal CCD detector/imager.

Figure 11:
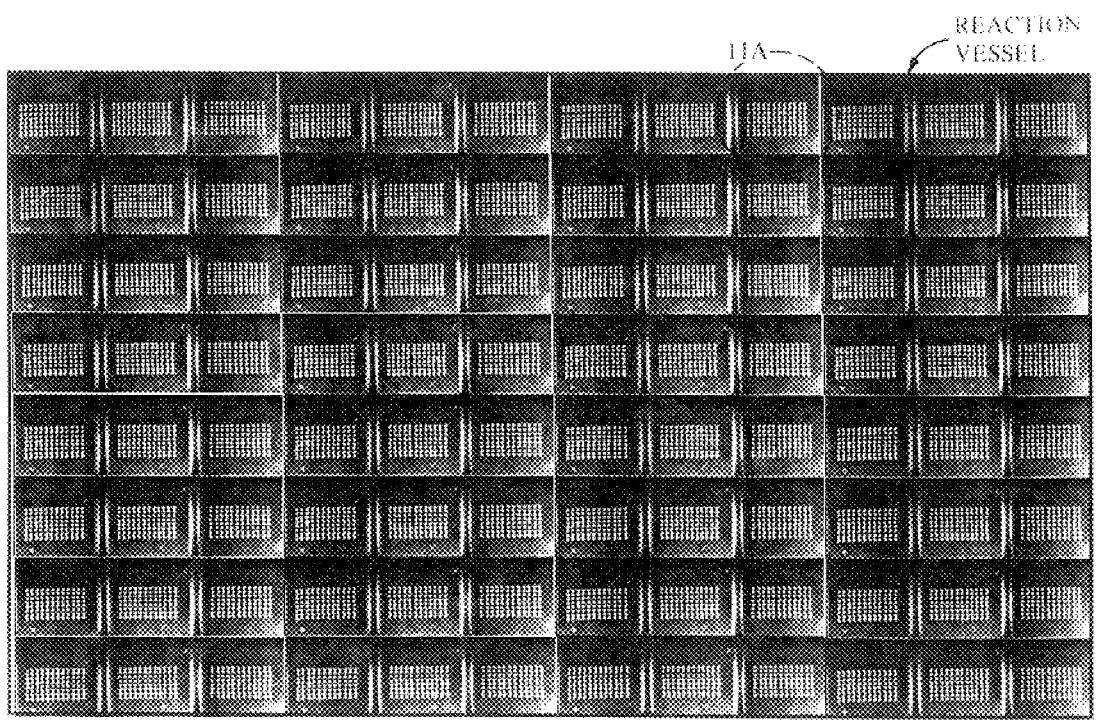
FIG. 11 is a printed computer image showing microarrays within a microplate reaction vessel. One single reaction chamber is shown as an insert.
Figure 11A:
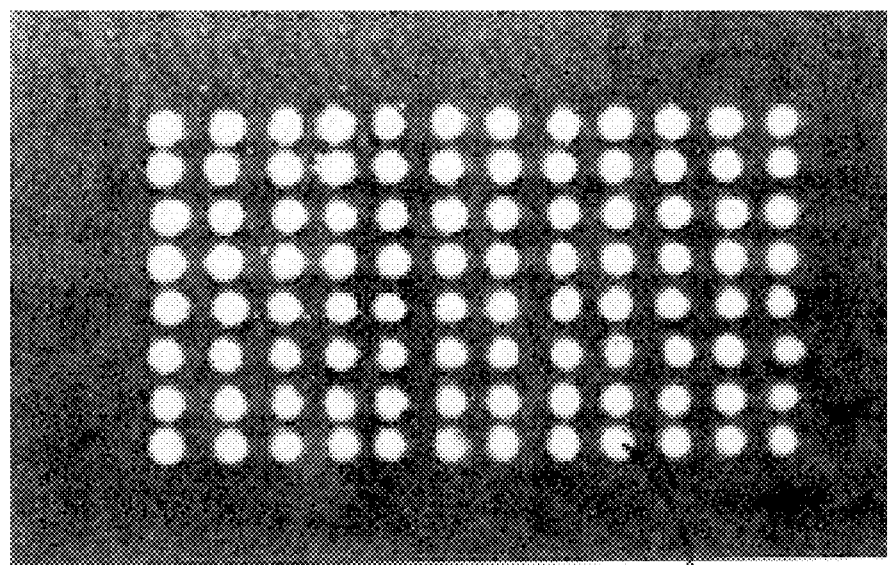

For example, each well or reaction chamber can contain 96 biosites as shown in FIG. 11. FIG. 11 is a printed computer image showing microarrays within a microplate reaction vessel. One single reaction chamber is shown as an insert. Thus, the reaction vessel essentially consists of microarrays within a microplate which cumulatively affords 9,216 (96×96) hybridization experiments per microtiter plate—a 100 to 1 multiplexing capacity.

The specific multiplexed microtiter plate reaction vessels to be used with proximal imaging are constructed by bonding thin films (typically glass or plastics) to conventional bottomless microtiter plates. All commercially available microtiter plates tested to date are incompatible to proximal imaging due to the thickness and composition of the bottom substrates.

The biosites are deposited by one of the several methods disclosed, either before or after the bottoms are bonded to the plate. In both situations, the probe molecules comprising the individual biosites must be attached to the glass or plastic surfaces.

In a preferred embodiment, thin (50–300 $\mu$m) vinyl substrates are amino or epoxy functionalized with silanes similar to glass substrates. Thin vinyl substrates are immersed in a 1–2% aqueous solution of polyvinyl alcohol at 65° C. The adsorbed polyvinyl alcohol is then reacted with either epoxy silane or amino silane, thus functionalizing the polymeric hydroxyl groups. Such optically clear vinyl substrates have the distinct advantage of blocking a large amount of the UV excitation source incident on the proximal CCD detector, but allowing the longer wavelengths (e.g. 500–650 nm) to pass through efficiently. This allows for greater sensitivity of labeled detector molecules that emit in such wavelength region.

Figure 12:
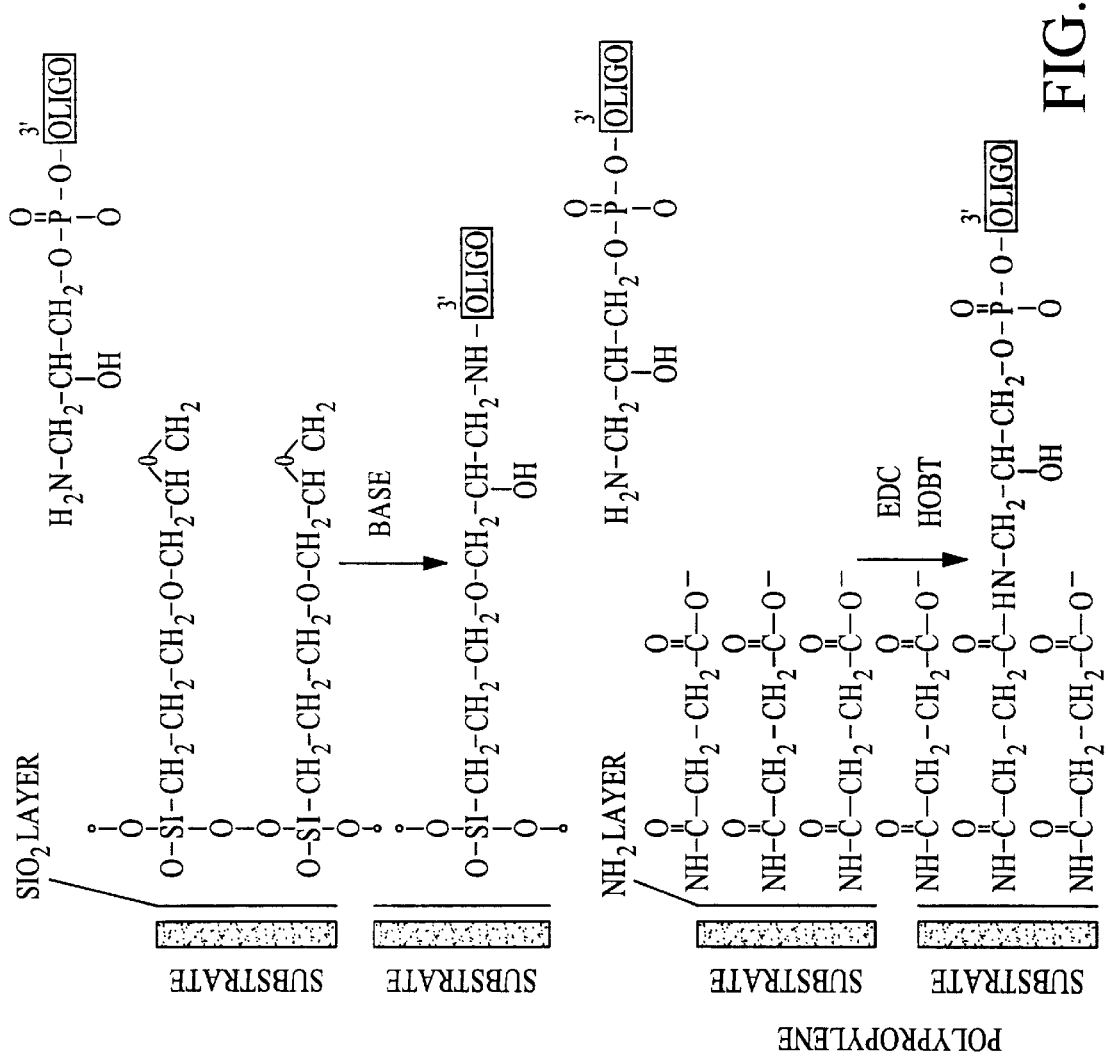
FIG. 12 is a diagram showing glass and polypropylene surface coupling chemistries.

Nucleic acid probe attachment to glass employs well-known epoxy silane methods (see FIG. 12) described by Southern and others (U. Maskos el al., *Nucleic Acids Res* (1992) 20:1679–84; S. C. Case-Green et al, *Nucleic Acids Res* (1994) 22:131–36; and Z. Guo et al., *Nucleic Acids Res* (1994) 22:5456–65). FIG. 12 is a diagram showing glass and polypropylene surface coupling chemistries. With 3' amine-modified probes, covalent surface densities can be obtained having $10^{11}$ molecules/mm$^2$ which is near the theoretical packing density limit. Amino-modified polypropylene is a convenient alternative to a glass substrate since it is inexpensive and optically clear above 300 nm. Amine-modified polypropylene can be converted to a carboxylic acid-modified surface by treatment with concentrated succinic anhydride in acetonitrile. Amine-modified probe is then coupled to this surface by standard carbodiimide chemistry in H$_2$O to yield probes at densities near $10^9$/mm$^2$ (see FIG. 12).

EXAMPLE III

USE—MULTIPLEXED DIAGNOSTICS

The multiplexed molecular analysis system can be employed for immunoassay and probe-based diagnostics. For immunoassays, the throughput of conventional ELISA assays can be increased with the multiplexed microplate format wherein a patient sample can be simultaneously interrogated by numerous antigens/antibodies within a single reaction chamber (well).

Similarly for probe-based diagnostics, target molecules derived from a patient sample can be dispensed into a single well containing numerous biosites for diagnosing genetic or infectious diseases. For example, single-stranded nucleic acid probes which are complementary to 96 known mutations of cystic fibrosis are arranged within a single well in a microplate. Upon hybridization with the patient's DNA sample, the resulting binding pattern obtained from the proximal CCD detector/imager indicates the presence of such known mutations.

The system can also be employed for high throughput, probe-based infectious disease diagnostics. Here the array of biosites within a single well in the microtiter plate can comprise DNA probes complementary to known viral strains. For example, a panel of probes (biosites) is arranged to diagnose a number of sexually transmittable diseases within a single well (reaction chamber). Consequently for a single microtiter plate, numerous patient samples can be simultaneously interrogated each against a panel of numerous probes to provide a very rapid, cost effective diagnostic testing platform.

Figure 13:
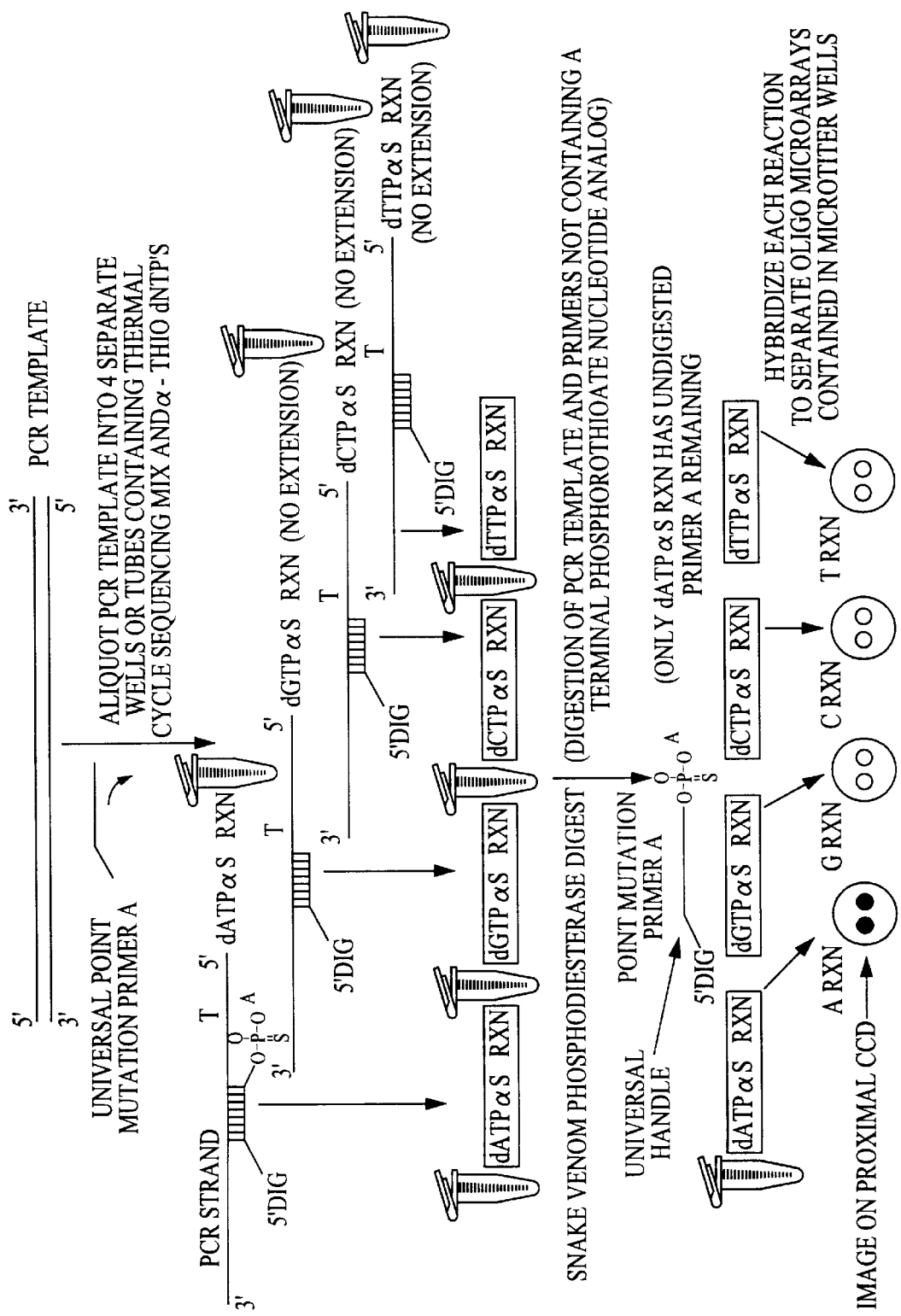
FIG. 13 is a diagram showing genotyping by universal point mutation scanning.
Figure 14:
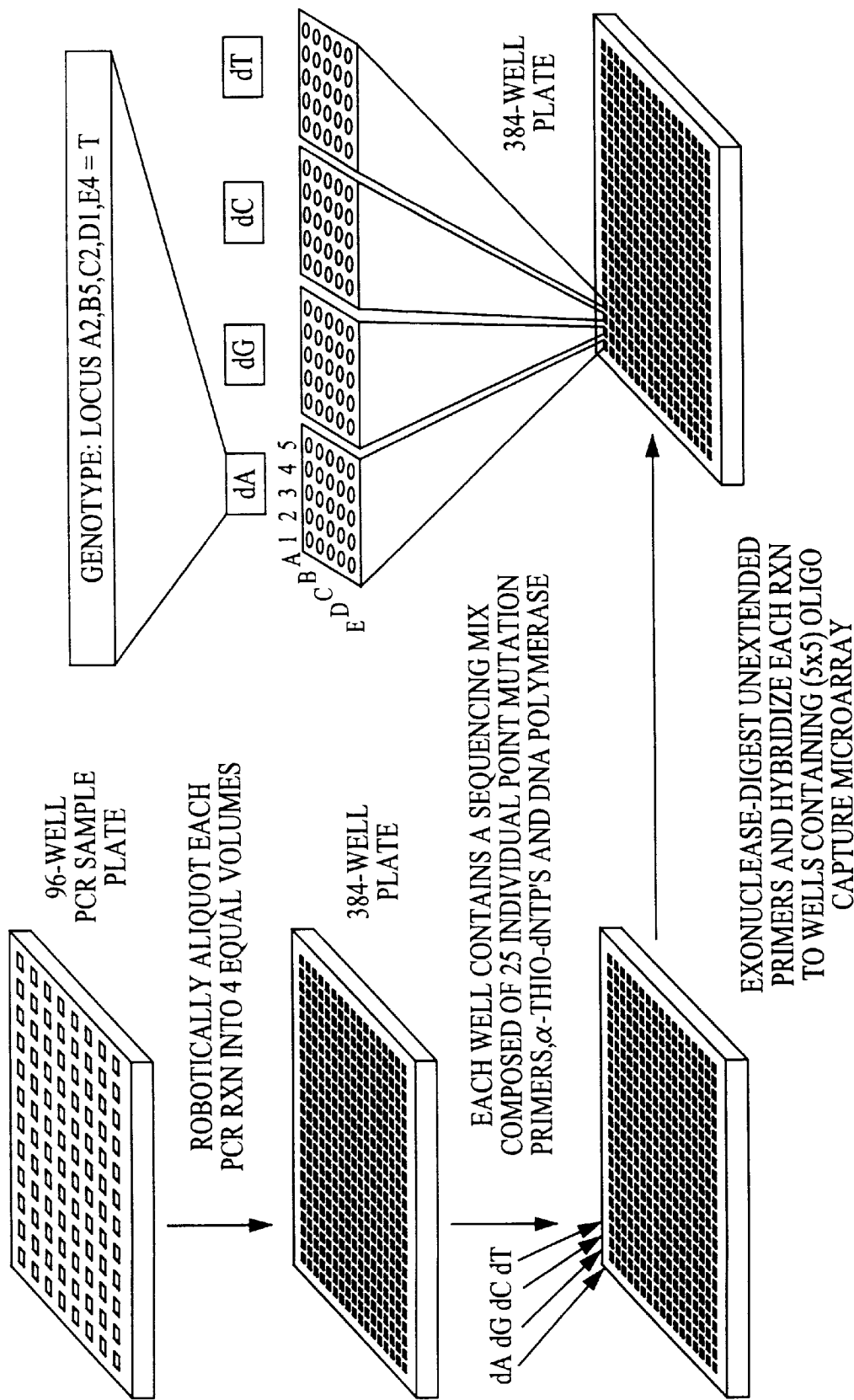
FIG. 14 is a diagram showing microtiter-based throughput genotyping.

Universal Arrays are perfectly suited for analysis and detection of multiple point mutations within a single PCR template. Often technical constraints are encountered when attempting to analyze multiple point mutations from a single PCR amplicon reaction. Most point mutation analysis techniques such as ribonuclease protection assay, SSCP, or CLEAVASE™ are well suited for detecting a single point mutation per amplicon or DNA template and require lengthy gel-based separation techniques. The simultaneous, rapid detection of numerous point mutations within a single PCR amplicon without an expensive, lengthy gel separation step is well beyond the capability of these technologies. Other newer, non-gel based technologies such as TAQMAN™ are also poorly suited for multiplexed analysis within a single reaction vessel. FIG. 13 illustrates the concept of using Universal Arrays for point mutation analysis (genotyping) at a single loci. FIG. 13 is a diagram showing genotyping by universal point mutation scanning. For example purposes only, FIG. 13 uses a single point mutation biosite to illustrate this type of analysis but could just as easily be simultaneously carried out on 25 different loci on a single PCR template as illustrated in FIG. 14.

Briefly, as shown in FIG. 13, the PCR template is aliquoted into 4 separate tubes (one for each dNTP) containing a standard sequencing mix, with the exception that dideoxynucleotides are not included. Instead, a single alpha-thio dNTP is substituted in each of the four separate mixes. Each mix also contains a single labeled primer with a universal sequence or "handle" at the 5' end which anneals just one nucleotide away from the mutation site on the PCR template (note: multiple primers each with unique universal sequences and complementary to different loci on the template is readily accomplished). After standard thermal cycle extension reactions are complete each tube is briefly incubated with snake venom phosphdiesterase. Only primers and templates that were not extended during the sequencing reaction are vulnerable to digestion by this 3'-specific exonuclease. Mutation primers containing a 3' thiophosphate ester linkage are highly resistant to digestion.

In this specific example, only the A reaction extended since a T was the next complementary base on the PCR template. Each digested, sequencing reaction mix in turn is then hybridized to four microtiter wells each containing identical immobilized microarrays complementary to the universal primer sequences. In this case, only the microtiter well hybridized to the A reaction mix gives a positive signal at a biosite loci complementary to the universal handle. In this fashion, up to 96 loci could be probed for point mutations on a single PCR template. Both strands in the PCR amplicon could be "scanned" in this manner simultaneously to allow more room for many primers to anneal without competition for the same hybridization loci on the template. In FIG. 13, "5-DIG" means 5' digoxigenin labeled.

For probe based diagnostics where both multiplexing within a single target molecule and low target concentrations are a problem, amplification with either PCR or LCR using the microtiter plate in a microtiter well concept conjoined to the Universal Array has distinct advantages. In a preferred embodiment, universal "handles" can be synthesized directly on the 5' end of Polymerase Chain Reaction or Ligase Chain Reaction primers and following in situ thermal cycling the amplified products can be simultaneously hybridized to 96 separate biosites. This format has other diagnostic advantages such as homogeneous detection of amplified products without having to open or expose the sample well to the ambient environment.

FIG. 14 is a diagram showing microtiter-based throughput genotyping. Briefly, FIG. 14 illustrates the concept of high throughput genotyping using microarrays. In practice, 96 separate PCR amplification reactions would be carried out using genomic DNA templates isolated from 96 different patient samples. The figure illustrates the concept of genotyping starting with 96 previously robotically purified PCR templates from these reactions. Each purified PCR product from each of the 96 wells is split into 4 separate aliquots/wells of a 384 well plate. Each well in this new plate would contain a pre-made sequencing buffer mixture, 25 individual primers, a thermostable DNA polymerase, and only one of the four αthio-dNTP's. The primers would anneal in a juxtaposed fashion to the PCR template just one nucleotide away from the nucleotide locus being genotyped. In each of the four wells, those primers juxtaposed next to the included nucleotide in the sequencing mix would be extended. Following the simultaneous extension of 384 reactions, each of the 384 wells is in situ digested with snake venom phosphodiesterase. Only primers in each reaction that had been extended by a single base are protected from digestion. All other DNA is degraded to mononucleotides. Following a brief thermal denaturation of the exonuclease, the contents of all the wells is robotically transferred to a new 384-well microtiter plate containing sequence complements microarrayed in a 5×5 microarray attached to the bottom of each well. Each of the 25 primers that had not been digested would hybridize to its corresponding complement in the array and imaged on the CCD detector to define the genotype at each loci.

Figure 15:
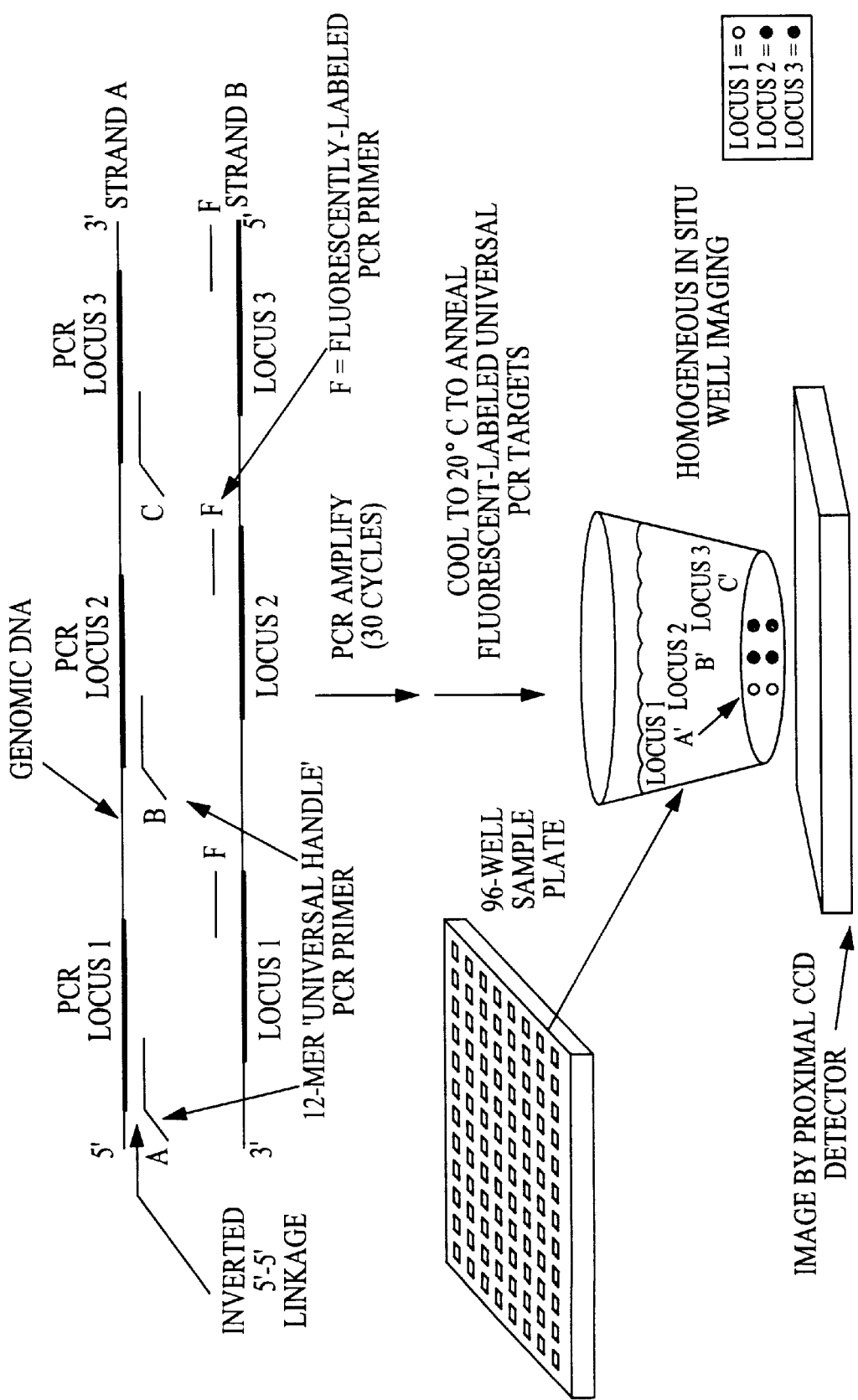
FIG. 15 is a diagram showing homogeneous in situ microarray detection of multiplexed PCR amplicons.

FIG. 15 illustrates this homogenous multiplexed approach for the Polymerase Chain Reaction (PCR) simultaneously at 3 different loci. FIG. 15 is a diagram showing homogeneous in situ microarray detection of multiplexed PCR amplicons. FIG. 15 illustrates specific multiplex hybridization detection of PCR products using microtiter-based microarrays. Briefly, in this figure three separate amplification loci are being detected simultaneously. Each locus (e.g, PCR LOCUS 1) is defined by two specially modified amplification primers that define the ends of the amplified PCR product. One primer in the pair, contains a fluorescently detectable label such as fluorescein. The other primer in the pair contains two domains, one is a unique universal sequence complementary to a capture probe arrayed at the bottom of a single microtiter well and the other domain specific for template amplification. The universal sequence is attached to the amplification primer in a 5' to 5' linkage so that when the polymerase is amplifying the region of interest it does not jump over this specialized juncture, leaving the universal sequence as a single stranded motif. If a particular template in a sample well being amplified contains both primer loci (i.e., detection and capture sites), then a PCR product will be generated that can simultaneously hybridize and be detected to a complementary member of a universal capture array by the CCD proximal detector. Since only PCR amplicons hybridized to members of the universal array at the bottom of each well are proximal to the detector, the assay requires no special separation step to detect hybridized amplicons and thus becomes homogenous in nature.

Figure 16:
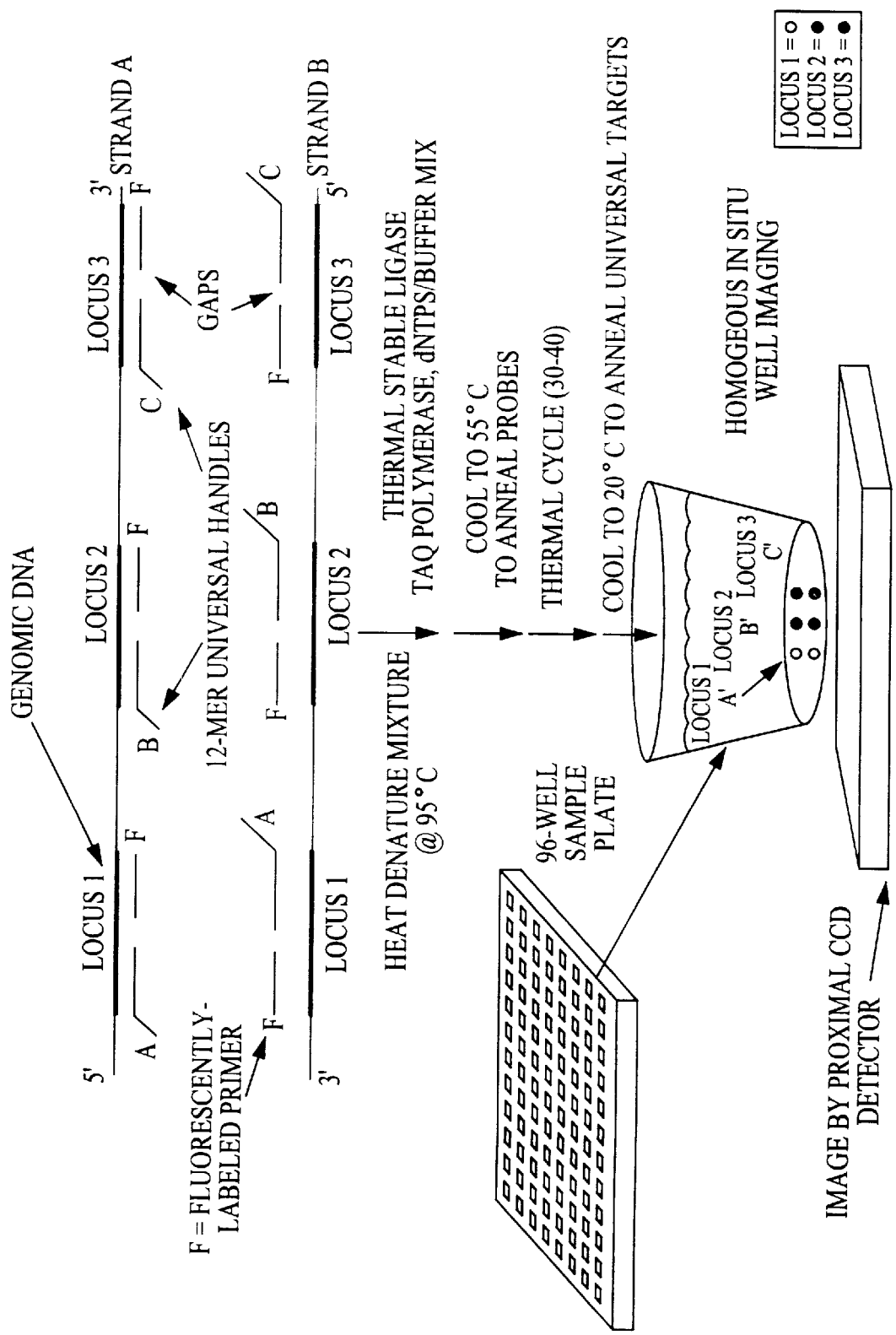
FIG. 16 is a diagram showing homogeneous in situ microarray detection of multiplexed gap-ligase chain reaction products.

Similarly, FIG. 16 illustrates this multiplexed concept with Gap-Ligase Chain Reaction (G-LCR). FIG. 16 is a diagram showing homogeneous in situ microarray detection of multiplexed gap-ligase chain reaction products. The ability to detect hybridization events homogeneously is provided by the fact that only molecules proximally associated with specific biosites can be imaged by the detector. FIG. 16 illustrates specific multiplex hybridization detection of Gap-Ligase Chain Reaction products using microtiter-based microassays. Similarly, as described previously for PCR products (see FIG. 15), this figure illustrates the assay at three separate ligation-dependent amplification loci simultaneously. Each locus (e.g., LOCUS 1) is defined by two specially modified primers that define the ends of the gap ligase chain reaction product. One primer in the pair, contains a fluorescently detectable label such as fluorescein. The other primer in the pair contains two domains, one is a unique universal sequence complementary to a capture probe arrayed at the bottom of a single microtiter well and the other domain is specific for a region on the template being detected. The universal sequence attached to this primer serves as a sequence specific single stranded handle. When the template is present in the sample then sequence directed ligation will join both the label and the universal handle into a single product. After many cycles this amplified ligated product can be simultaneously hybridized and detected to its complementary member on a universal capture array immobilized to the bottom of a microtiter well and imaged by the CCD proximal detector. Since only ligated products hybridized to members of the universal array at the bottom of each well are proximal to the detector, the assay requires no special separation step to detect hybridized amplicons and thus becomes homogenous in nature.

EXAMPLE IV

DRUG DISCOVERY/SCREENING ANALYSIS

In this example, a small molecule Universal Array could use high affinity, commercially available antibodies to numerous haptens, steroids, or small molecule drugs. A partial list of 48 representative compounds are enumerated in Table 1 for which specific antibodies are available. This table is only a partial list of commercially available antibodies to haptens, steroid hormones and other small molecule drugs.

TABLE 1

| fluorescein | dinitrophenol | amphetamine | barbiturate |
|---|---|---|---|
| acetaminophen | acetohexamide | desipramine | lidocaine |
| digitoxin | chloroquinine | quinine | ritalin |
| phenobaribital | phenytoin | fentanyl | phencyclidine |
| methamphetamine | metaniphrine | digoxin | penicillin |
| tetrahydrocannibinol | tobramycin | nitrazepam | morphine |
| Texas Red | TRITC | primaquine | progesterone |
| bendazac | carbamazepine | estradiol | theophylline |
| methadone | methotrexate | aldosterone | norethisterone |
| salicylate | warfarin | cortisol | testosterone |
| nortrptyline | propanolol | estrone | androstenedione |
| digoxigenin | biotin | thyroxine | triiodothyronine |

Small molecule Universal Arrays are made by covalent attachment of small molecules such as those found in Table 1 to substrate surfaces. Immobilization of haptens, steroids, or drugs is accomplished by introducing a functionalized moiety at one end of the small molecule. These moieties are well known to those skilled in the art (e.g. N-hydroxy-succinimide, maleimide, isothiocyanate, iodoacetamide or other amine or sulfur reactive moieties). Small functionalized molecules or drugs can then be reacted with $NH_2$ or $SH_2$ derivitized plastic or glass substrates. Some specific examples of such commercially available activated haptens include NHS-fluorescein, NHS-biotin, NHS-digoxigenin, maleimide-biotin, and maleimide-tetramethylrhodamine.

Following deposition of the individual small molecule biosites, a bispecific ligand can be used to spatially localize specific binding events to given biosites. The bispecific ligand can comprise, but is not limited to, antibody-antibody conjugates, antibody-receptor, antibody-streptavidin, antibody-peptide, antibody-small molecule conjugates or bispecific antibodies.

Figure 17:
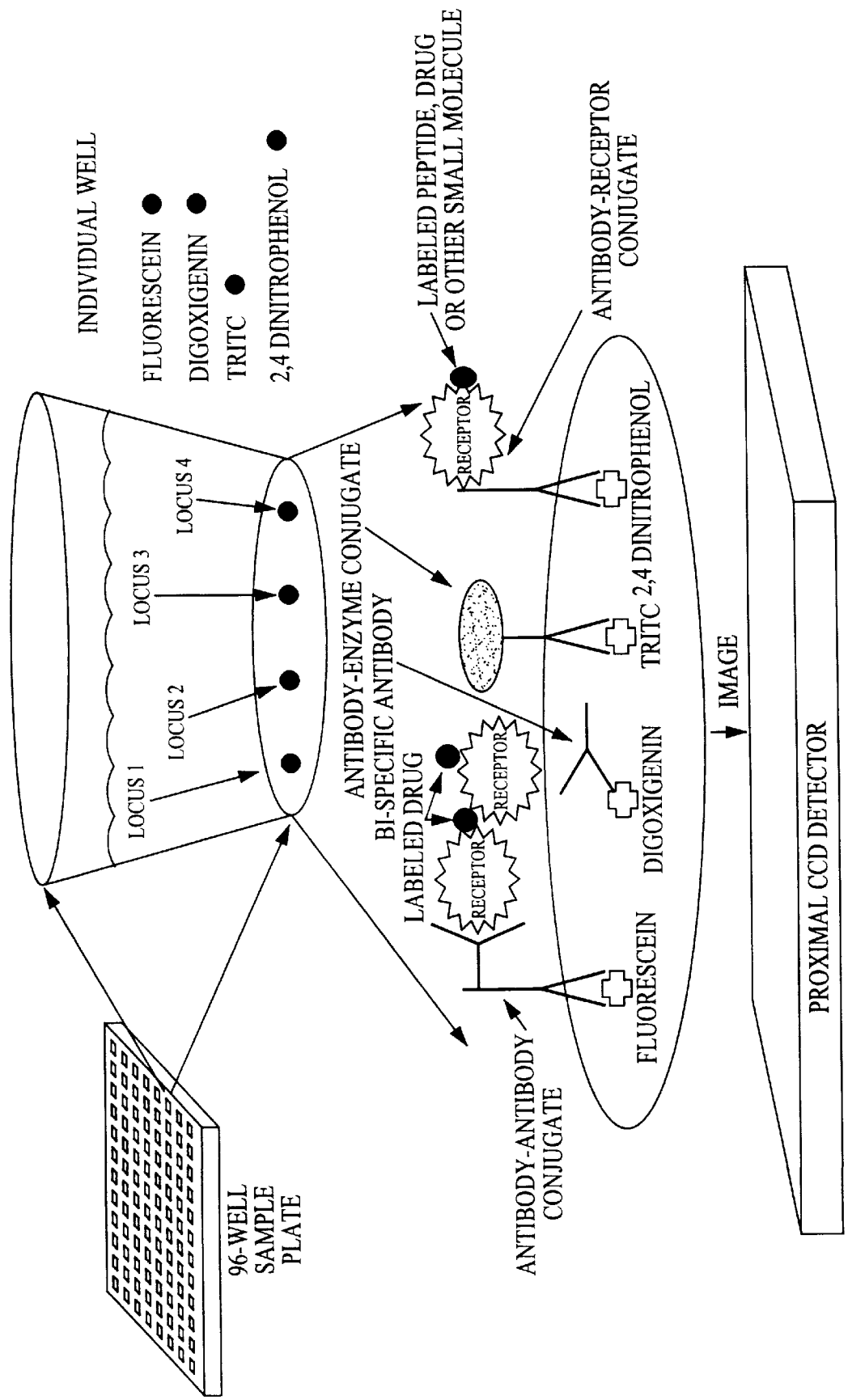
FIG. 17 is a diagram showing small molecule universal array (drug screening/discovery).

The bispecific ligand is specific to both the immobilized hapten or drug on the substrate surface (biosite) and the analyte being screened. Examples of Universal Array screening are diagramed in FIG. 17. FIG. 17 is a diagram showing small molecule universal array (drug screening/discovery). FIG. 17 illustrates the basic small molecule Universal Array concept using four different immobilized haptens in a single well. Various bispecific molecules are diagramed for illustration purposes. FIG. 17 illustrates four separate and distinct haptens immobilized at the bottom of each of 96 wells of a microtiter plate. Each locus or biosite in the array is defined by four unique immobilized haptens illustrated in this example by fluorescein, digoxigenin, 2,4 dinitrophenol, and TRITC. Bispecific molecules uniquely specific for both the immobilized hapten and another labeled analyte in the sample are added to each well. In this fashion, different multiple analytes can be simultaneously detected and their presence indicated by signals at specific hapten biosites. In this example, 96 individual samples can be assayed for four different analytes simultaneously. As shown, the fluorescein biosite detects a labeled receptor (protein) analyte, both the 2,4 dinitrophenol and digoxigenin haptens allow for the simultaneous detection or presence of two additional types of protein receptors in the sample. Finally, the TRITC hapten allows for detection and presence of a specific enzyme substrate via an intervening enzyme conjugate. Once again, the proximal mode of detection allows for homogenous imaging of only those binding events at the surface of the array. The advantages of such a multiplexed immunological approach is the exquisite specificity and variety of small molecules that comprise such a Universal Array using non-DNA based recognition of biosites.

Actual reduction to practice of small molecule Universal Arrays is illustrated in FIGS. 18 and 19 and described in Example I above.

EXAMPLE V

USE—GENE EXPRESSION ANALYSIS

The multiplexed molecular analysis system is also useful for analyzing the expression of hundreds of different mRNA species in a single tissue sample within a single well of a microtiter plate. Here synthetic nucleic acids form the distinct biosites which constitute numerous highly sensitive and selective hybridization analyses per sample, employing only 50 µL of sample extract. Such massive hybridization analyses enables the discovery and employment of numerous biomarkers for specific diseases such as cancer. Essentially, the search for biomarkers of early phase lung cancer becomes an iterative, combinatorial process. For lung cancer and other epithelial disease, several hundred mRNAs are analyzed for their value as biomarkers at relatively low cost. In such an iterative process, the biostatistician becomes the end-user of the technology and a central component in the development of the final set of mRNA biomarkers. Once an mRNA biomarker set is discovered by this iterative approach, the technology is naturally suited for low cost, high throughput screening of large patient populations with the mRNA biomarker set of choice.

EXAMPLE VI

USE—CELL SORTING

Conversely, intact cells are analyzed utilizing the multiplexed format of this invention. Specifically, most "cell enrichment" protocols involve either double label flow cytometry, or physical separation of cells via affinity chromatography of some kind. Both require access to an antibody which is specific to the cell type of interest.

In a multiplexed microplate format, the cell-specific antibodies are arranged in a matrix fashion within the reaction chamber (single well in the 96 well microplate). The key to making the cellular analysis work is creating a situation wherein such antibody arrays retain the capacity for high affinity and high selectivity binding of intact cells.

The procedure is to add a complex cellular mixture, e.g., a biological sample (for example, blood or sputum), to such an antibody matrix, then with some local mixing, allowing the cells to bind to the surface. If cells bind to such a matrix with good affinity and selectivity, they are then fixed to the matrix, permeabilized, and subjected to labeled probe hybridization (or PCR) in a fashion which is nearly identical to the methods which are currently used to analyze DNA or RNA in cells for microscopy or flow cytometry.

The principle benefit of the multiplexed format is that many different cell types are separated in a single well of a microtiter plate.

EXAMPLE VII

USE—MICROORGANIC MONITORING

Microorganism monitoring applications can also be addressed by the multiplexed molecular analysis system. In particular for monitoring air, water, and food for microorganisms, the system can rapidly and cost effectively provide detection and quantification of complex biological mixtures. An example would be a ribosomal RNA probe-based assay in which nucleic acid probes serving as the biosites are chosen to selectively capture RNA of characteristic microorganisms.

Basically, the procedure is initiated by preparing the microbial rRNA sample for hybridization to the biosite array within the reaction chamber. Following specific binding of the fluorescently labeled microbial RNA to the probe array, a two dimensional image results that uniquely characterizes the sample. The analyzer output is the microbial spectrum, consisting of the amount and type of microorganisms present in the sample.

The rationale for the proposed approach to simultaneous monitoring of microorganisms includes:

1) Fast microbial analysis can be achieved due to the avoidance of standard cell cultivation procedures which require days to perform. Moreover, the proposed highly sensitive proximal CCD detection procedure, combined with the inherent amplification property of rRNA, reduces the combined sample preparation, assay, and detection time from days to hours.

2) Simultaneous microbial monitoring can be achieved due to the high density arrays that support hundreds of immobilized probes per $cm^2$ to facilitate multiple microorganism detection and identification in a high throughput manner.

3) Minimal labor and training is required since no cell culturing or gel-based sequencing is required. Instead, an operator merely subjects the prepared sample to automated hybridization, washing, and drying processes to obtain the microbial spectrum.

4) Minimal equipment is necessary since the probe-based assay is integrated with the proximal CCD detection device, thereby alleviating traditional macro-detection techniques such as epifluorescent and confocal microscopy.

The following references may facilitate the understanding or practice of the certain aspects and/or embodiments of this invention. Inclusion of a reference in this list is not intended to and does not constitute an admission that the reference represents prior art with respect to the present invention.

Hansell, U.S. Pat. No. 2,512,743

D. Bogg, F. Talke, *IBM Jour. Res. Develop.* (1984) 29:214–321

Burke, el al., "An Abuttable CCD Imager for Visible and X-Ray Focal Plane Arrays," *IEEE Trans. On Electron Devices*, 38(5):1069 (May, 1991).

Maskos, U., et al., *Nucleic Acids Res.* 20:1679–1684 (1992).

Stephen C. Case-Green, et al., *Nucleic Acids Res.* 22:131–136 (1994).

Guo, Z., et al., *Nucleic Acids Res.* 22:5456–5465 (1994).

A number of embodiments of the present invention have been described. Nevertheless, it will be understood that various modifications may be made without departing from the spirit and scope of the invention. Accordingly, other embodiments are within the scope of the following claims.

What is claimed is:

1. A device for preparing a reaction substrate having biosites for conducting multiplexed microassays to determine binding between a target analyte and a capture probe, including:
   a plurality of capillary tubes, each tube having a proximal end and a distal end;
   an attachment site for holding said capillary tubes at a point spaced from the distal ends of such capillary tubes;
   an array template for slidably holding each capillary tube near its distal end, and for allowing the distal end of each capillary tube to move with respect to the attachment site;
   at least one manifold for positioning the proximal end of each capillary tube within a corresponding supply chamber, wherein each supply chamber is capable of supplying a liquid reagent to at least one corresponding capillary tube; and
   a positioning device for precisely positioning the array template and said capillary tubes with respect to said reaction substrate and depositing liquid reagents from said distal end of said capillary tubes onto said reaction substrate as biosites.

2. The device of claim 1, wherein said plurality of capillary tubes comprises about 2 to about 10,000 tubes, having a center to center spacing of about 80 $\mu$m to about 5 mm.

3. The device of claim 1, wherein each supply chamber supplies only one capillary tube.

4. The device of claim 1, wherein a supply chamber supplies a plurality of capillary tubes.

5. The device of claim 1, wherein said capillary tubes comprise stainless steel, plastic, rubber, glass, or fused silica coated with polyimide.

6. The device of claim 1, wherein said device includes a plurality of array templates.

7. The device of claim 1, further comprising a positioning device for precisely positioning said reaction substrate.

8. The device of claim 1, wherein said capillaries have an inside diameter of about 10 to about 200 $\mu$m, and an outside diameter of about 80 to about 500 $\mu$m.

9. The device of claim 1, wherein said array template comprises an array of sleeves, each sleeve having an inside diameter sufficient to permit a capillary to slide through, and a length sufficient to allow a precise pattern to be maintained while depositing fluids onto said reaction substrate.

10. The device of claim 1, wherein said array template comprises a plurality of holes formed in a rigid material.

11. The device of claim 1, wherein said array template comprises a rigidly formed or held mesh.

12. The device of claim 1, further comprising a housing for containing said supply chambers.

13. The device of claim 12, wherein said housing is capable of maintaining an inert atmosphere.

14. The device of claim 12, wherein said housing is capable of maintaining an elevated or reduced temperature.

15. The device of claim 12, wherein said housing may be pressurized to a predetermined pressure.

16. The device of claim 15, wherein said pressure is modulated to control the flow of liquid reagents through said capillary tubes.

17. The device of claim 1, wherein said supply chambers are positioned higher than the distal end of said capillary tubes to provide a pressure head.

18. The device of claim 1, wherein deposit of liquid reagent is controlled by a means for electrophoresis.

19. The device of claim 1, wherein deposit of liquid reagent is controlled by a means for electro-osmosis.

20. The device of claim 1, wherein said device includes multiple sets of supply chambers, each for supplying liquid reagent to a subset of said capillary tubes.

21. The device of claim 1, wherein said capillary tubes are free to flex between said attachment site and said array template.

22. The device of claim 1, wherein the reaction substrate is pre-etched to define a pattern of reactive areas matching the geometry of the deposited biosites.

23. The device of claim 1, wherein said biosites are deposited substantially simultaneously.

24. The device of claim 1, wherein each biosite is fluidically isolated from each other biosite.

25. The device of claim 1, wherein the liquid reagent comprises at least one capture probe.

26. An apparatus for preparing a reaction substrate for use as an assay device, including:
   an attachment site for holding a plurality of flexible capillary tubes at a point spaced from the distal ends of such capillary tubes;
   a structure for positioning the proximal end of each capillary tube within a corresponding supply chamber, each supply chamber capable of supplying a liquid reagent to at least one corresponding capillary tube;
   a print head for holding said plurality of capillary tubes near their distal ends and for precisely positioning the distal ends of said capillary tubes with respect to said reaction substrate to deposit liquid reagents onto said reaction substrate as biosites.

27. The apparatus of claim 26, where the print head includes an ink-jet deposition device.

* * * * *